United States Patent [19]
Morrison et al.

[11] Patent Number: 6,099,864
[45] Date of Patent: Aug. 8, 2000

[54] IN SITU ACTIVATION OF MICROCAPSULES

[75] Inventors: Dennis R. Morrison, Kemah; Benjamin Mosier, Houston, both of Tex.

[73] Assignee: The United States of America as represented by the Administrator of the National Aeronautics and Space Administration, Washington, D.C.

[21] Appl. No.: 09/079,741

[22] Filed: May 15, 1998

Related U.S. Application Data

[63] Continuation-in-part of application No. 08/349,169, Dec. 2, 1994, Pat. No. 5,827,531.

[51] Int. Cl.[7] .................................................. A61K 9/50
[52] U.S. Cl. .......................... 424/489; 424/423; 424/450; 428/402.2; 428/402.21; 264/4.1; 264/4.3; 264/4.32; 264/4.33; 514/951
[58] Field of Search ..................... 424/450, 489, 424/423; 428/402.2, 402.21; 264/4.1, 4.3, 4.32, 4.33

[56] References Cited

U.S. PATENT DOCUMENTS

| | | | |
|---|---|---|---|
| 4,532,123 | 7/1985 | Gardner et al. | 424/21 |
| 4,898,734 | 2/1990 | Mathiowitz et al. | 424/426 |
| 4,933,185 | 6/1990 | Wheatley et al. | 424/461 |
| 5,417,982 | 5/1995 | Modi | 424/486 |
| 5,433,955 | 7/1995 | Bredehorst et al. | 424/94.3 |
| 5,470,582 | 11/1995 | Supersaxo et al. | 424/489 |

*Primary Examiner*—James M. Spear
*Attorney, Agent, or Firm*—James M. Cate

[57] ABSTRACT

Disclosed are microcapsules comprising a polymer shell enclosing two or more immiscible liquid phases in which a drug, or a prodrug and a drug activator are partitioned into separate phases, or prevented from diffusing out of the microcapsule by a liquid phase in which the drug is poorly soluble. Also disclosed are methods of using the microcapsules for in situ activation of drugs, where upon exposure to an appropriate energy source the internal phases mix and the drug is activated in situ.

76 Claims, 1 Drawing Sheet

IN SITU ACTIVATION OF MICROCAPSULES

CROSS-REFERENCE TO RELATED APPLICATIONS

This application is a continuation-in-part of U.S. patent application Ser. No. 08/349,169 filed Dec. 2, 1994 (now U.S. Pat. No. 5,827,531); and this application is related to the following U.S. Patent Applications which are filed contemporaneously herewith:

(1) Application Ser. No. 09/079,833 entitled "Microencapsulation and Electrostatic Processing Device" invented by Dennis R. Morrison, Benjamin Mosier and John M. Cassanto, NASA Case No. MSC-22937-1-SB;

(2) Application Ser. No. 09/079,758 entitled "Externally Triggered Microcapsules" invented by Dennis R. Morrison and Benjamin Mosier, NASA Case No. MSC-22939-1-SB;

(3) Application Ser. No. 09/079,770 entitled "Low Shear Microencapsulation and Electrostatic Coating Process" invented by Dennis R. Morrison and Benjamin Mosier, NASA Case No. MSC-2293 8-1-SB.

(4) Application Ser. No. 09/079,766 entitled "Microencapsulated Bioactive Agents and Method of Making" invented by Dennis R. Morrison and Benjamin Mosier, NASA Case No. MSC-22836-1-SB;

STATEMENT REGARDING FEDERALLY SPONSORED RESEARCH OR DEVELOPMENT

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The invention relates to methods for making microcapsules, encapsulating pharmaceutical compounds in microcapsules, microcapsules, microcapsule encapsulated pharmaceutical compositions and products, and methods of using these compositions.

2. Description of the Related Art

Many cytotoxic or bioactive drugs and enzymes cannot be injected intravenously. Others can be injected, but are rapidly degraded before they reach the target tissue. Still others are cleared from the blood by the liver or kidneys so quickly that their biological half-life is too short to be of therapeutic value. Still other drugs are insoluble in aqueous solutions. Since intravenous injection in hydrocarbon solvents is not well tolerated by patients, such drugs are difficult to administer.

One method for overcoming these limitations is encapsulation into microcapsules or liposomes. Encapsulation of drugs or biological therapeutics into liposomes or liquid microcapsules can enable delivery to target organs where the bioactive drug can be released directly by diffusion. Properly designed microcapsules can provide unique methods of direct delivery by parenteral injection, nasal inhalation and dermal administration for sustained release of important bioactive drugs.

Major difficulties with commercial preparation of microcapsules arise when density-driven phase separation of the immiscible carrier fluids occurs. This is especially true when the microcapsules are constructed by forming water/oil emulsions or when attempts are made to encapsulate multiple drugs. This limits the yield and often results in microcapsules that are not spherical nor uniform in size. Nonconformity limits the packing density (and, thereby, the drug payload delivered) when the microcapsules arrive at the target tissues.

Certain current methods of forming microcapsules (such as liposomes) are based on chemical characteristics of certain phospholipids that self-assemble into bilayers when dispersed in an excess of water. Most liposomes carry pharmaceuticals dissolved in the entrapped water phase. Drugs that are insoluble or that have only limited solubility in aqueous solvents pose problems for incorporating into liposomes. Such organic-soluble drugs are usually limited in liposomal formulations to those that bind inside the hydrophobic region of the liposome bilayer. Some drugs are so insoluble that they do not associate with the bilayer and, therefore, have very low encapsulation efficiencies. Certain liposomal drug formulations, including anti-tumor liposomes containing doxorubicin [Gabizion et al. 1992] or muramyltripeptide have been studied extensively in clinical trials.

Microcapsule formation by liquid-liquid dispersion of aqueous drugs and organic solvents typically produces water-in-oil, (W/O) type liposomes. A second requisite step is removal of the organic solvent (typically evaporated) to form reverse-phase evaporation vesicles (rev) or stable plurilamellar vesicles (splv).

Spherical multilamellar vesicles (mlv) are rarely formed by these methods and the size distribution is quite heterogeneous. Typically, in order to generate multilamellar vesicles, film casting techniques with organic solvents, hydration and sizing using filtration through inert membrane filters are required [Talsma and Crommelin 1992]. Methods of forming multi-layered microcapsules often require emulsification of the aqueous phase into organic carrier solutions by shear, bubbling or sonication. Sophisticated, multi-step emulsion technology is required and yields of uniform type and size are often very low.

Liquid microemulsions also have been developed as drug delivery systems, especially for drugs that are poorly soluble in aqueous carriers. A microemulsion typically contains droplets in the range of 0.1–1 $\mu$ in diameter. Such microemulsions are characterized by very fluid and dynamic micelles which are formed by sequential mixing of one immiscible phase with another using surfactants and co-surfactants [Bhargava et al. 1987]. Typically, surfactants that produce water-in-oil (W/O) microemulsions have a hydrophilic-lipophilic balance (HLB) rating of 3 to 6, while those that produce oil-in-water (O/W) microemulsions have an HLB of 8 to 18. The surfactants can be non-ionic, ionic, or amphoteric. Often, medium chain-length alcohols are added as the co-surfactant in the last step in achieving the final microemulsion.

A disadvantage of microemulsions is that each micelle (liquid capsule) is too small (typically, less than 1.0 micron) for deposition in larger vascular beds when administered by intravascular injection. Therefore, microemulsions are not suitable for chemoembolization type treatment of vascularized tumors. Additionally, since microemulsions are true colloidal suspensions, they cannot be scaled up to large enough size for many intravascular drug delivery applications. Microemulsions formed with lipid soluble anti-tumor agents and low density lipoproteins (LDLS) have been used to target drugs to neoplastic cells that require large amounts of cholesterol for synthesis of cell membranes [Halbert et al. 1984]. However, LDLs also attract phagocytes making the amount of drug actually delivered to the tumors and thence the therapeutic dose difficult to determine.

The use of solid matrix microspheres containing adsorbed drugs within the matrix is also known. For instance, U.S. Pat. No. 4,492,720 to Mosier disclosed methods for making microspheres to deliver chemotherapeutic drugs (including Cis-Platinum) to vascularized tumors. This method of preparing microspheres is accomplished by liquid encapsulation and solid-phase entrapment wherein the water-soluble drug is dispersed in a solid matrix material. The method involves dissolving the aqueous drug and the matrix material in an organic solvent, in which they are mutually soluble, then dispersing this mixture in a second organic solvent to form an emulsion that is stable enough for intravascular injection.

Other approaches have utilized copolymers such as polyvinyl chloride/acrylonitrile dissolved initially in organic solvents to form microcapsules containing, for instance aqueous enzyme solutions. U.S. Pat. No. 3,639,306 to Sternberg et al. discloses a method of making anisotropic polymer particles having a sponge-like inner support structure comprising large and small void spaces and an outer, microporous polymer film barrier. A multiple-step batch process is used which entails removal of the organic solvents used to dissolve the polymers prior to addition of aqueous components. Solid-matrix microspheres, however, are often not perfect spheres thereby limiting the packing density. Additionally, many drugs cannot be trapped or adsorbed in these systems at effective concentrations and drug-release rates are often not constant.

Conventional methods of forming multi-lamellar, immiscible, liquid microcapsules are limited, because of density-driven phase separation and stratification into horizontal layers resulting in the necessity to use multi-step, batch processing including mechanical mixing and solvent evaporation phases [Talsma and Crommelin 1992]. Each batch step suffers losses which reduce overall efficiencies. Conventional solvent evaporation methods do not permit simultaneous formation of the outer skin as the microcapsule itself is formed. Many conventional therapeutic microcapsules or liposomes have natural phospholipid outer skins (usually in combination with cholesterol and a fatty amine such as stearylamine) and therefore are subject to elimination by immune cells. Other conventional methods use sialic acid and other coatings on the lipid bilayer to mask the liposomes from detection by the scavenging systems of the body. Without an adequate outer skin, microcapsules often coalesce thereby reducing shelf-life.

For instance, U.S. Pat. No. 4,855,090 to Wallach, discloses a method of making a multilamellar lipid vesicle by blending an aqueous phase and a nonaqueous lipophilic phase using a high shear producing apparatus. The lipophilic phase is maintained at a high temperature (above the melting point of the lipid components) and is combined with an excess of the aqueous phase, which is also maintained at a high temperature. U.S. Pat. No. 5,032,457 to Wallach discloses a paucilamellar lipid vesicle and method of making paucilamellar lipid vesicles (PLV). The method comprises combining a nonaqueous lipophilic phase with an aqueous phase at high temperatures and high shear mixing conditions, wherein the PLVs are rapidly formed in a single step process. These methods do not, however, include internal mixing of immiscible phases inside the PLV's after they are formed.

U.S. Pat. No. 4,501,728 to Geho et al. discloses the encapsulation of one or more drugs or other substances within a liposome covered with a sialic acid residue for masking the surface of the membrane from scavenging cells of the body utilizing techniques known for the production of liposomes. In one embodiment, additional tissue specific constituents are added to the surface of the liposome which cause the liposome thusly treated to be attracted to specific tissues. Similarly, U.S. Pat. No. 5,013,556 to Woodle et al. provided methods for making liposomes with enhanced circulation times. Liposomes created by this method contain 1–20 mole% of an amphipathic lipid derivatized with a polyalkylether (such as phosphatidyl ethanolamine derivatized with polyethyleneglycol). U.S. Pat. No. 5,225,212 to Martin et al. discloses a liposome composition for extended release of a therapeutic compound into the bloodstream, the liposomes being composed of vesicle-forming lipids derivatized with a hydrophilic polymer, wherein the liposome composition is used for extending the period of release of a therapeutic compound such as a polypeptide, injected within the body. Formulations of "stealth" liposomes have been made with lipids that are less detectable by immune cells in an attempt to avoid phagocytosis [Allen et al. 1992]. Still other modifications of lipids (i.e., neutral glycolipids) may be affected in order to produce anti-viral formulations. U.S. Pat. No. 5,192,551 to Willoughby et al. 1993. However, new types of liposomes and/or microcapsules are needed to exploit the various unique applications of this type of drug delivery.

Liquid microcapsules and liposomes can provide effective drug delivery by intravascular injection, nasal inhalation and dermal administration for sustained release of bioactive chemicals. However, drug delivery of bioactive drugs, or enzymes or biocatalysts entrapped in liquid microcapsules and liposomes are limited to those biochemicals whose useful biological shelf-life typically is more than a year. Many bioactive drugs possess chemical or bioactive half-lives which last only days. Microencapsulation has been used to greatly extend the normal two-hour half-life of labile enzymes to prolong the effective half-life up to 70 hours after injection (Chang, 1971). However in that instance, the active drug is encapsulated, rather than the inactive prodrug form, since it is difficult to chemically alter a drug once it has been encapsulated. Short-lived drugs could be effectively delivered inside microcapsules if a method of encapsulating a long-lived precursor drug form can be combined with a method for the in situ conversion of the precursor to the short-lived active form, just prior to, or even after administration.

Controlled release of drugs from liposomes has been achieved by using temperature sensitive polymers in the formation of the liposomes (Magin et al. 1986). Once the liposomes are localized in the target tissue (or tumor) the drug can be rapidly released if the local tissue temperature can be raised above the transition temperature of the liposome membrane. This requires some method of controlled tissue heating which is difficult to achieve without complicated surgical procedures, implanted interstitial antennas or ultrasonics to produce effective local hyperthermia (Hand, 1991). However, there is no method of activating a prodrug or predrug in a liposome using electromagnetic energy and/or ultrasound.

In a controlled delivery system described by Supersaxo et al. in U.S. Pat. No. 5,470,582, pore-containing microcapsules are preformed of polymers such as polyesters, polyamides, polyanhydrides and polyacrylates and an active agent is allowed to migrate into the microcapsules through the pores. After administration, the active agent is released through the pores by diffusion. A burst of release may be caused by application of ultrasonic radiation. Another system, described by Mathiowitz et al. in U.S. Pat. No. 4,898,734, is also based on passive or facilitated diffusion of an active agent from pore-containing polymer microcapsules. Methods of facilitating diffusion include exposure to high temperature, light, or ultrasound. This patent also describes degradable microcapsules and microspheres immobilized in a polymer matrix. A controlled release delivery system described by Modi in U.S. Pat. No. 5,417,982 is biodegradable copolymer based microcapsules in which delayed release of an active agent is controlled by the time required for enzymatic digestion of the polymer matrix. Wheatley et al. describe in U.S. Pat. No. 4,933,185, microcapsules having an inner core and an outer, ionic skin. An active agent and an enzyme are encapsulated in the inner core, such that the enzyme degrades the inner core and releases the active agent. All the carrier systems described in this paragraph encapsulate the active agent rather than a prodrug, and thus do not overcome the limitations of administering short-lived active agents as described above.

A method of in situ activation of a prodrug is described in U.S. Pat. No. 5,433,955, issued to Bredehorst et al. This method is a two step process in which an activator bound to a targeting moiety is administered to a subject. In a second step, the prodrug is released into the circulation and becomes activated only where the activator is bound. A disadvantage of this method is, because neither the activator nor the drug are encapsulated or enclosed in a carrier, the activator substance is exposed to the serum of a subject and may contact a substrate prior to reaching its target site, thus causing possible side effects. In addition, unbound activator must be cleared from the system prior to administration of the second agent. Also care must be taken to avoid immunological reactions to both the activator and the prodrug.

It is evident, therefore, that improvements are still needed that address certain drawbacks of conventional liposome or microcapsule delivery systems as well as those of in situ drug activation. For example, conventional liposomes or microcapsule delivery systems are only useful for drugs with a long shelf life or biological activity. If the bioactive form of the drug is short lived or chemically labile, the effective shelf life of the encapsulated drug may make it impractical for normal pharmaceutical storage. In addition, delivery of an active drug to a specific site in the body with a liposome formulation still presents difficulties. There is a need for a type of microcapsule delivery system that is stable for long term storage and that preferably would be able to contain both a drug precursor and the activator for that precursor so that activation of the precursor to its active form can take place just prior to administration, or even after administration and confirmation that the drug delivery system (microcapsules) is in the desired location. Even more advantageous would be the ability to specifically activate only that portion of the delivery system that is in the desired location. Finally, there is a need to be able to accomplish all that without physiological changes or damage in the surrounding healthy tissue.

BRIEF SUMMARY OF THE INVENTION

The present invention addresses these and other drawbacks in the prior art by providing microcapsules containing drugs, drug precursors, prodrugs or other agents that can be activated in situ by the application of an external energy source. It is a surprising discovery of the present inventors that microcapsules as disclosed herein, when exposed to a source of energy such as ultraviolet light, undergo vigorous internal mixing for as long as they remain in the light. Because the microcapsules contain immiscible internal liquid phases, such as aqueous phases and organic (hydrocarbon or oil) phases, different chemical or biological agents can be kept separated inside the microcapsules by their respective solubilities in the different phases, and then brought into contact by the physical mixing induced by irradiating the capsules. This mixing may occur, of course, outside the body, or it may be induced inside the circulatory system or tissues of a human, thus providing controllable in situ drug activation.

An embodiment of the invention is the ability to encapsulate a pro-drug or drug precursor and an activator of the drug with a different solubility in separate liquid phases within the microcapsules. Another embodiment is the ability to sequester a prodrug in an internal liquid phase that is not in contact with the polymer shell, and then activate the prodrug into an active form with a different solubility such that the active drug is associated with the internal liquid phase that is in contact with the polymer shell. In this way, the prodrug is inhibited from diffusing out of the microcapsule, but the active drug is not. This embodiment is made possible by the disclosure herein of microcapsules in which an organic or aqueous phase can be made to form a concentric layer just inside the polymer shell and surrounding one or more immiscible phases within the microcapsule.

Another embodiment of the invention arises from the ability to form small spheroids within the microcapsules. These spheroids remain in a plane and resemble what is termed a "string of pearls" conformation. These spheroids provide a method of sequestering an agent away from the outer polymer shell as well as away from an activator contained in an internal liquid phase outside the spheroids. These spheroids may be disrupted by ultrasound, for example, to release the contents into the microcapsules for activation and/or diffusion.

The present disclosure provides specific advantages over prior methods of drug storage and delivery in that a microcapsule may be provided in which a short-lived drug may be stored as a precursor for an extended period of time and activated just prior to use by the application of an appropriate energy. The energy may be applied ex vivo by exposing a solution containing microcapsules to a light or other form of energy, or the microcapsules may be administered to a subject, allowed to reach a desired target, detected at the target site and then activated by application of energy. In either case, it is an advantage that the active drug remains in the microcapsule until activated, and is released at the desired site of action. This aspect of the microcapsule delivery systems disclosed herein offers a clear advantage over methods in which an active drug is injected into the circulation of the subject where it may cause side effects and/or immunological responses prior to reaching its target site.

Another advantage offered by the present disclosure includes compositions and methods for the delivery of labile drugs, activated enzymes, and other drugs that normally become inactivated while en route to the target tissue or by long term storage. Examples include the delivery of active enzymes that autocatalyze upon storage for several weeks, such as plasminogen activator and other enzymes used to dissolve fibrin clots. In light of the present disclosure, one may now encapsulate these unstable agents in their inactive and more stable forms because one can activate the drugs by energy sources outside the microcapsule just prior to administration, or even after the microcapsules have been introduced into a body and detected at the desired target site. Another embodiment includes the activation of a chemical agent such as a drug or active enzyme precursor by electromagnetically induced mixing of two or more precursor components dissolved in different immiscible-liquid phases. The mixing of the two phases then allows the precursor and activator to react to form the active agent within the microcapsule, thus allowing for a practical way to store and deliver short-lived active drugs where normal shelf life is too short for typical storage in medical clinics or hospitals, for example.

Other advantages offered by the present disclosure include the co-encapsulation of an energy absorbing medium that permits drug activation just prior to administration or at prescribed times after microcapsule deposition in a target tissue to allow for the development of novel therapy regimens. This embodiment is applicable to improving the efficacy of some types of photodynamic therapies wherein the photoactive drug, absorbed into tumor cells is activated by visible to near infrared light at e.g. 630 nm for hematoporphyrin esters, or benzoporphyrins at around 690 nm to cause the release of free radicals, thus destroying vascular cells within the tumor.

The present disclosure also provides the ability to use flow-through activating devices to transmit electromagnetic, sonic, or microwave energy through the microcapsules described herein as the microcapsules pass through such devices in a fluid suspension. In this embodiment, the deposition of external energy activates a prodrug inside the microcapsules or causes physical mixing of reactants contained in different immiscible phases inside the microcapsules to accelerate activation kinetics, thus producing active drug just prior to use.

Certain embodiments of the invention may be described as methods of in situ activation of a drug comprising providing a microcapsule wherein the microcapsule comprises two or more immiscible liquid phases enclosed in a polymer shell, a drug precursor contained in at least one of the immiscible liquid phases and, in certain embodiments, an energy absorbing medium, and the method further comprises exposing the microcapsule to an electromagnetic field or other source of energy in an amount effective to activate the drug precursor to obtain an active drug.

It is a further aspect of this embodiment that the active drug may then diffuse out of the polymer shell. The polymer shell is designed so that it is transparent to the particular energy source to be used, but is permeable to the active drug, but may not be permeable to the drug precursor. In certain embodiments this is accomplished by designing the microcapsules so that the active drug is not soluble, or is poorly or sparingly soluble in the liquid phase in contact with the polymer shell. In the practice of the invention, the prodrug may be activated by a variety of means, including a change in pH, dehydrogenation, hydrolysis, oxidation, reduction, by enzymatic or other catalytic reaction, through direct absorption of energy such as light, or contact with free radicals, superoxides, ions or gases such as carbon dioxide, nitrogen, etc. that may be encapsulated in the microcapsules, or may be provided externally or by catheter in in vivo applications.

Examples of such agents or drugs that may be used in the practice of the invention include, but are not limited to drugs in which the prodrug is preferentially soluble in an aqueous phase and the active drug is preferentially soluble in a hydrocarbon phase such as cocaine hydrochloride, which is activated to cocaine base for use as a local anesthetic; floxuridine (2'-deoxy-5-fluorouridine, which is activated to fluorouracil (5-fluoro-2,4(1H,3H) pyrimidinedione), an anticancer agent; sulfamerazine sulfate, which is activated to sulfamerazine base (2-sulfanilamido-4-methyl pyrimidine), an antimicrobial agent; scopolamine, which is activated to scopine by pancreatic lipase; plant alkaloids such as yohimbine, or quinine HCL, for which the activated form is preferentially soluble in a hydrocarbon or oil phase. This type of embodiment would also include some fat or oil soluble steroids or hormones that have an inactive water soluble form including testosterone acetate, which is activated to testosterone; pregnenolone, which is activated to progesterone; and estrone, which is activated to estradiol.

In certain embodiments, the prodrug is preferentially soluble in a hydrocarbon or oil phase and the active drug is preferentially soluble in an aqueous phase. Such embodiments would include, but not be limited to papaverine, which is activated to papaverine hydrochloride, which is useful as an antispasmodic in arterial smooth muscle; genoscopolamine, which is reduced to scopolamine; hematoporphyrin, activated to di-hematoporphyrin ester by weak acid; and quinidine, activated to quinidine hydrochloride or quinidine sulfate, useful as a treatment for auricular fibrillation. Various sterols may be included in such embodiments, as they may be precipitated from a hydrocarbon layer by association with urea, substituted urea, bile salts, glycerol, saponins, digitonin, maleic anhydride, citraconic anhydride, etc.

Activators of prodrugs that may be included in the microcapsules would include any of such activators known in the art, and would include, but not be limited to reducing agents, such as sodium borohydrides, inorganic catalysts such as zinc dust, oxidizing agents such as benzoyl peroxides, enzymes, and particularly enzymes that retain high activity in strongly dehydrating or hydrocarbon systems or in the interfaces of hydrocarbon and aqueous phases, such as liver esterases, pancreatic lipases, and enzymes associated with hepatic microsomes, for example, as well as any appropriate water soluble enzymes, such as serine proteases, useful to activate urokinases, thrombolytic enzymes, and plasminogen activators, etc. In certain embodiments, floxuridine may be directly converted to the inhibitor of thymidilate synthetase, fluoro-deoxyuridine monophosphate (F-dUMP) by thymidine kinase within the microcapsules for use in chemotherapy of certain cancers.

In certain other embodiments, one may use a prodrug that is activated by the direct absorption of light energy, such as ergosterol, which is activated by 300 nm ultraviolet light to vitamin $D_2$ (calciferol), or 7-dehydrocholesterol, which is activated by 280–300 nm ultraviolet light to vitamin $D_3$.

It is another aspect of this embodiment that one may include an activator contained in an immiscible liquid phase other than the phase containing the drug precursor and wherein the activator is effective to activate the precursor to an active drug upon contact. The activator may be an agent that alters the drug precursor either physically, chemically or both so that the precursor becomes activated. In certain embodiments, the activator may be oxidized or otherwise altered by the absorption of energy to become activated, or in alternative embodiments, the prodrug may absorb the energy and be transformed into an active agent.

In certain embodiments of the invention the electromagnetic energy is effective to cause the liberation of free radicals or ions from a component within the microcapsule, including the contents of the liquid phases or, in some embodiments, the polymer shell. Collisions of these charged species with the activator then alter the activator so that it is effective to activate the prodrug or agent in the microcapsules. Alternatively, the electromagnetic energy may be absorbed by the prodrug itself, thereby converting the prodrug to its active form.

It is a discovery of the present inventors that a microcapsule as described herein has the property that the absorption of energy, such as ultraviolet light, may cause a mixing of the immiscible liquid phases and thus, an activator and a drug precursor that are separated into two immiscible liquid phases may be brought into contact within the microcapsule through this mixing action. The energy may be administered ex vivo, as in a solution or a suspension of the microcapsules, or the microcapsule may be administered to an animal subject or even a human subject and the energy may be applied to the subject, either through the skin or outer layers of the body or an organ, or intravascularly by a catheter, for example. It is understood that in the practice of the invention the microcapsules may be administered through intraarterial, intravenous, or intraperitoneal administration, or alternatively, administration may also be topical, intradermal, nasal, oral, anal, or vaginal as determined by the preferred site of action. In any case, the microcapsules may be delivered to the site of disease and to reside adjacent or in contact with a disease site when the energy is applied.

In those embodiments of the invention in which the microcapsules are within the body of a subject, the energy may be applied using an intravascular device, such as a catheter containing or adapted to contain a fiber optic conductor, antennae, or transducer, for example as is well known in the art. It is understood that such devices may be inserted intravenously, intraarterially or through a surgical opening and directed to microcapsules contained in an organ or circulatory system and energy such as light, electromagnetic, radiofrequency, microwave, or even ultrasound energy may be directed through the device fitted with an appropriate conductor such as a fiber optic conductor in the case of light energy. The conductor is typically connected to an energy source that is external to the body, but in certain instances, for example when using electromagnetic energy, the energy may be applied via an electromagnetic transducer contained in the lumen or attached to the surface of a catheter.

In certain embodiments of the invention, the microcapsules may also contain a radiocontrast media, or a medium that becomes radio-opaque through a change of oxidation state when exposed to energy such as discussed above. The radiocontrast media to be used may include, but is not limited to a halogenated oil, such as for example, halogenated poppy seed oil, cotton seed oil, soybean oil, safflower oil, corn oil, olive oil, sunflower seed oil, sesame seed oil, or canola oil.

The microcapsules of the invention can be separated by filtration or other means known in the art to obtain a population of microcapsules of a particular size range that is preferred for a particular use. The size and shape of the microcapsules is a factor in the distribution and drug delivery in the tissues. Typically, microcapsules of 1–20 micron diameter are optimum for intravenous administration, whereas, 50–300 micron diameter microcapsules are used for intraarterial chemoembolization delivery and 300 micron or greater for intraperitoneal administration. In each size range, highly uniform microcapsules are preferred for maximum packing densities and maximum drug payload delivery to target organs or tumors.

Therefore, one may obtain microcapsules of from about 1 to about 500 microns in diameter, or from about 300 to about 500 microns in diameter, or from about 50–300 microns in diameter, or from about 30 to about 50 microns in diameter, or from about 20 to about 30 microns in diameter, or even from about 1 to about 20 microns in diameter. As is known in the art of chemo-embolization, particles of a certain size will form a part of an embolization in different areas such as the arterial, lung capillaries, venous, or even peritoneal systems of a body. Microcapsules may be designed, then to be used in a chemo-embolization application, or they may be designed to pass freely through the capillaries or circulation of a subject in order to reach a target site. In the practice of the invention, one may choose microcapsules of a particular size so that the microcapsules will occlude an arterial or venous vessel, for example at the site of a disease. Such a disease site may be a thrombosis, a wound, a site of infection, a lipid deposit or even the vasculature of a tumor.

The drug precursors of the present invention are in certain cases a proenzyme or a zymogen. A proenzyme is an inactive enzyme precursor that can be activated by cleavage of one or a few specific peptide bonds. In certain embodiments the proenzyme may be a pro-thrombolytic enzyme, or a pro-urokinase, or a pro-tissue plasminogen activator. In certain embodiments the prodrug may be one that stimulates fibronectin and other attachment proteins for use in wound healing, for example.

Other types of drugs or bioactive agents useful in the microcapsules disclosed herein include, but are not limited to anesthetics, systemic antibiotics, antiparasitics, systemic quinolones, anti-infectives, anti-inflammatories, aminoglycosides, cephalosporins, penicillins, antidotes, anti-cholinesterases, metal poisoning antidotes, antineoplastics, 5'-fluorouracil, cytotoxic agents, hormones, steroids, immunomodulators, cytokines, systemic antivirals, systemic antifungals, biologicals, alpha-antitrypsin, bone metabolism regulators, hypercalcemic agent, cardiovascular agents, beta blockers, cerebral vasodilators, cerebral metabolic enhancers, cholinesterase inhibitors, colony stimulating factors, granulocyte-colony stimulating factors, granulocyte macrophage-colony stimulating factors, vasopressors, local diabetic agents, diagnostics such as CT scan enhancers and angiocardiography agents, adenosine deaminase deficiency agents, gonadotropin inhibitors, adrenal cortical steroid inhibitors, gonadotropin releasing hormone stimulant, urofollitropins, muscle relaxants such as neuromuscular blocking agents, prostaglandin analogs, prostaglandins, prostaglandin inhibitors, respiratory therapy agents, anticholinergics, beta andrenergic stimulators, sympathomimetics, and thrombolytics.

Certain embodiments of the invention will include the use of fluorinated pyrimidine or purine analogs such as the prodrug Floxuridine (Fluorodeoxyuridine) which is converted to fluorouracil (5-FU). Other embodiments may utilize the oxidation, reduction or hydrolysis of a prodrug that results in activation, change in activity or in conformation. Another example may be the use of the prodrug 6-mercaptopurine, which is activated to 6-mercaptopurine ribonucleotide, the oxidation of trimethadone to the active agent, dimethadione, the oxidation of phenacetin to methemoglobin, or the reduction of chloral hydrate to trichloroethanol. In addition, active agents may be produced in microcapsules by contact with lipid soluble enzymes such as those isolated from the hepatic microsomes, or they may use doxorubicin derivatives activated by lysozyme.

The energy to be used in the practice of the invention may be any form of energy for which an energy absorbing medium may be included in the microcapsules, and would include, but would not be limited to light, an electromagnetic field, sonic, or microwave energy. In certain embodiments the microcapsules may be exposed to ultraviolet light, visible light, near infrared light, radiofrequency, or microwave, in particular, infrared light of about 600–900 nanometer wavelength, ultraviolet light of about 220–390 nanometer wavelength or any of these in combination with ultrasound of greater than 18 KHz.

In certain embodiments, activation of a drug precursor will involve a change in molecular conformation, ionization state, oxidative state, or surface charge (zeta potential), to produce the active drug. In addition, the activation may also alter the hydrophilic/lipophilic balance, thereby causing the drug to more readily diffuse out of the polymer shell of the microcapsule, or into tissue, or to change its clearance time. All such changes in a drug or precursor are included within the scope and spirit of the present invention as defined by the appended claims.

An embodiment of the present invention is a micromixer useful for mixing two or more immiscible liquid phases comprising a microcapsule comprising two or more immiscible liquid phases enclosed in a polymer shell and an energy absorbing medium; and an energy source compatible with the energy absorbing medium. By a compatible energy source and energy absorbing medium, it meant that the medium is capable of absorbing the energy source used. For example, a chromophore or other material that absorbs light of a certain wavelength would be compatible with an energy source that includes light at that wavelength. Or a medium that absorbs radio waves of a certain frequency would be compatible with a source of energy at that frequency. It is also understood that the materials used to construct the microcapsules and including the oils and liquids comprising the immiscible phases may also serve as energy absorbing media.

The micromixers of the present disclosure will have other uses that may be practiced by those in the art. For example, one may place microcapsules in a solution, such as blood, serum, or other solution that contains a water soluble element that one wants to remove, such as a toxin. In the practice of this embodiment, the water soluble element would be allowed to diffuse across the polymer shell into an aqueous layer in the microcapsule. The microcapsules would contain an element that absorbs or binds the toxin in a liquid layer immiscible with the aqueous layer. After an appropriate time for diffusion, the energy source is applied, thus mixing the contents of the microcapsule and causing the toxin to be removed from solution. The microcapsules can then be removed by centrifugation, filtering, or other means. In those embodiments in which ferromagnetic particles are included in the microcapsules, separation may be accomplished by exposing the solution to a magnetic field.

The present inventors have demonstrated that microcapsules as described herein, when exposed to an energy source such as ultraviolet light exhibit high velocity flows within the microcapsules that appear to result in mixing of the immiscible liquid phases contained in the microcapsules. As an aspect of the present invention, the kinetic energy produced in the microcapsules disclosed herein may be harnessed as a micro or nano-engine for use in a micro machine or micro mixer application. For example, the microcapsules may be placed in a solution that allows the diffusion of certain chemical agents or proteins into the capsules and then irradiation may mix those chemicals with other agents contained in an immiscible liquid phase within the microcapsules, thus altering the osmotic or ionic balance of a solution and creating a gradient, which can be used as a switching device to activate a chemical cascade, for example. In alternate embodiments, PEG-diacrylate may be gelled by the action of irradiated eosin-Y thus trapping solubilized agents in the solution.

The micromixer may utilize any source of irradiation or energy such as electromagnetic fields and ultrasound. More particularly it may utilize ultraviolet light, near infrared light, radiofrequency, or microwave. In certain embodiments, the inventors have demonstrated for example the use of ultraviolet light of 330–390 nanometers wavelength. In certain embodiments the immiscible liquid phases are further defined as comprising at least one aqueous phase and at least one hydrophobic or organic phase, where one or more of the immiscible liquid phases may contain a drug precursor.

An embodiment of the present invention may also be described as a method of treating a thrombus or embolus in an animal subject comprising providing a microcapsule wherein the microcapsule comprises two or more immiscible liquid phases enclosed in a polymer shell, a pro-thrombolytic enzyme contained in a first liquid phase, immiscible with a second liquid phase, a thrombolytic enzyme activator in the second immiscible liquid phase and an energy absorbing medium; and exposing the microcapsule to energy that is absorbed by the energy-absorbing medium in an amount effective to activate the pro-thrombolytic enzyme to obtain an active thrombolytic enzyme; wherein the active thrombolytic enzyme diffuses out of the microcapsule and digests or lyses the thrombus or embolus. In the practice of this embodiment, the absorption of energy has been demonstrated to cause a mixing of the immiscible liquid phases. In addition the microcapsules may also contain a radiocontrast media, such as a halogenated oil or other halogenated compound. Examples of oils that may be used include poppy seed oil, cotton seed oil, soybean oil, safflower oil, corn oil, sunflower seed oil, sesame seed oil, or canola oil.

In the treatment of a fibrin clot which partially occludes a blood vessel, the attending physician may first infuse microcapsules as described herein into the vascular circulation of a subject, for example, and allow the microcapsules to be carried to the site of the clot. The microcapsules are sized to form an embolism at the site and thus to be relatively immobilized. As such, depending on the site of the thrombosis, one may use microcapsules of from about 1 to about 500 microns in diameter, or from about 300 to about 500 microns in diameter, or from about 50 to about 300 microns in diameter, or from about 30 to about 50 microns in diameter, or from about 20 to about 30 microns in diameter, or even from about 1 to about 20 microns in diameter. The presence of a radiocontrast agent such as an unsaturated oil allows the physician to visualize the microcapsules at the disease site. The physician may then apply the energy source so that the pro-fibrinolytic or thrombolytic enzymes in the microcapsules become activated and diffuse out of the polymer shell to attack the thrombosis. The energy can be applied through the least invasive manner, such as by using a catheter, or an antennae, if possible. The art of manipulating catheters that are inserted into a vein or artery and controlled from outside the body is a well developed the field and is easily applicable to the present invention. Typically a catheter contains or defines a lumen and one may insert a conductor such as a fiber optic conductor through the lumen of a catheter to illuminate or irradiate a site at the distal end. Alternatively, other forms of energy may be used either from an external energy source conducted through a catheter, or through the skin or external layers of an organ, or the energy source, such as an electromagnetic transducer may be contained in or on a catheter or other intravascular device. Energy sources that may be used in the practice of the invention include, but are not limited to light, an electromagnetic field, sonic, or microwave energy. In certain embodiments the microcapsules may be exposed to ultraviolet light, visible light, near infrared light, radiofrequency, or microwave, in particular, infrared light of about 600–900 nanometer wavelength, ultraviolet light of about 220–390 nanometer wavelength or any of these in combination with ultrasound of greater than 18 KHz. Pro-enzymes that may be effective in the practice of this embodiment include any enzyme that is capable of dissolving or decreasing a clot, or thrombosis and would include, but not be limited to pro-urokinase pro-tissue plasminogen activator, procathepsin B, or plasminogen.

Embodiments of the present invention include compositions for long term storage of labile compounds such as labile enzymes. Many labile enzymes are known in the art and would be useful in the present invention, an example of a type of enzyme is the cholinesterases. Such compositions may comprise a precursor of a labile enzyme contained in a microcapsule wherein the microcapsule comprises two or more immiscible liquid phases enclosed in a polymer shell, and further wherein the precursor of a labile enzyme is contained in a first liquid phase and an activator of the labile enzyme is contained in a second liquid phase immiscible with the first liquid phase and the composition is contained in a light protective container. The container may also be protective of other forms of radiative energy as well. In the practice of this embodiment, the inactive form of a labile enzyme or compound may be kept in storage for an indefinite period of time before the contents are exposed to an energy that will activate the enzyme for use.

An embodiment of the invention is also a pharmaceutical composition comprising a microcapsule comprising two or more immiscible liquid phases enclosed in a polymer shell, a drug precursor and a drug activator, wherein the drug precursor and drug activator are contained in separate immiscible liquid phases and further wherein the microcapsule is contained in a pharmaceutically acceptable carrier solution. Pharmaceutical compositions may contain anti-cancer drug precursors, anti-infective drugs, hormones, thrombolytic drugs and cholesterolases, for example.

In those embodiments in which the microcapsules contain an anti-tumor drug, or pro-antitumor drug, the invention may be described as a method of treating a tumor in a subject comprising obtaining a pharmaceutical composition comprising a plurality of microcapsules, each microcapsule comprising two or more immiscible liquid phases enclosed in a polymer shell, an anti-cancer drug precursor and a drug activator, wherein the anti-cancer drug precursor and drug activator are contained in separate immiscible liquid phases and further wherein the microcapsules are contained in a pharmaceutically acceptable carrier solution; administering the pharmaceutical composition to the subject in a manner effective to place the microcapsules within or adjacent to the tumor; and exposing the microcapsules within or adjacent to the tumor to ultraviolet, infrared, electromagnetic, microwave energy, or ultrasound effective to mix the immiscible liquid phases containing the anti-cancer drug precursor and the drug activator; where upon mixing, the drug activator contacts the anti-cancer drug precursor and produces an active anti-cancer drug, and further where the active anti-cancer drug diff-uses out of the polymer shell and contacts the tumor. An example of this embodiment would be the use of floxuridine, which is 7–10% soluble in an organic phase, as a precursor to the active anti-cancer drug, 5-flourouracil.

In those embodiments in which the microcapsules are used in the treatment of a human, such as a cancer patient, or cardiac patient, for example, it is understood that, where appropriate, the treatments disclosed herein may be used successfully in conjunction with other forms of chemotherapy, hyperthermia therapy or even photodynamic therapy as described in Horspool and Song (Eds.) CRC Handbook of Organic Photochemistry and Photobiology, CRC Press, NY, 1994, for example.

As described herein the inventions of the present disclosure may be compositions comprising a microcapsule comprising two or more immiscible liquid phases enclosed in a polymer shell, a drug precursor and a drug activator, wherein the drug precursor and drug activator are contained in separate immiscible liquid phases and further wherein the microcapsule is made by the method comprising: formulating a first phase comprising a first solvent, a first polymer soluble in the first phase and insoluble in a second phase, a co-solvent, oil, and water, formulating the second phase immiscible with the first phase, the second phase comprising a second solvent, a second polymer soluble in the second phase and insoluble in the first phase, a surface active agent, and a salt; the surface active agent having a hydrophilic/lipophilic balance value greater than that of the first polymer; the second polymer having a hydrophilic/lipophilic balance value lower than that of the surface active agent; creating an interface between the first and second phases in a manner that limits fluid shear to between about 10 to 50 dynes/cm$^2$, if carried out under conditions of greater than or about equal to 1 gravity, or between about 2 to 30 dynes/cm$^2$, if carried out under conditions of less than or about equal to $1 \times 10^{-2}$ gravity, and maintains adsorptive surface characteristics at the interface.

Processes and compositions are provided by the present invention which overcome certain of the limitations of prior methodology for forming microcapsules. In particular, methods and compositions are provided which form multi-lamellar microcapsules having alternating hydrophilic and hydrophobic liquid layers, surrounded by flexible, semi-permeable hydrophobic, outer membranes which can be tailored specifically to control the diffusion rate. In particular, the methods of making microcapsules provided by the present invention do not rely on batch processes such as density-driven phase separation and stratification into horizontal layers, mechanical mixing or solvent evaporation. Encapsulation of cytotoxic or labile drugs in such microcapsules enables targeted delivery and sustained release kinetics that are not currently available with intravenous injection.

The invention provides, in one aspect, methods of making a multi-layered microcapsule. The term microcapsule as used herein is a general term which can include any spherical microscopic vesicle including microspheres, micelles, inverted micelles, bilayer vesicles and liposomes. The term microcapsule as used herein is also a more specific term which refers to a microcapsule which comprises at least two layers, one of which is innermost and is substantially completely enclosed within the other. In a distinct break from traditional methods for making microcapsules, the methods of the invention rely on low fluid shear, differential surface tension, interfacial coacervation, and liquid-liquid diffusion process, particularly as developed for forming microcapsules that may contain both aqueous and hydrocarbon soluble drugs.

The terms multi-layered and multi-lamellar are used interchangeably throughout the specification and claims and both refer to the fact that the microcapsules of the invention comprise at least two immiscible layers nested around one another. In some instances, the core layer will be hydrophobic in nature and will be completely surrounded by at least one neighboring hydrophilic layer. In others, the core layer will be hydrophilic in nature and will be completely surrounded by at least one neighboring hydrophobic layer.

The basic method of the invention relies on liquid-liquid interactions. In the basic method, the first step entails formulating a first phase or layer while the second step entails formulating a second phase or layer. The two phases or layers are formulated to be immiscible with one another. For the purposes of this invention, "immiscible" means that due to differences in density, viscosity or surface tension, the two adjoining phases or layers form an interface resembling a meniscus, and furthermore that the solubility of any component in one phase is not more than 10 gm/100 ml in the second, adjoining phase or layer.

Formulating the first phases or layer comprises combining a first solvent, a first polymer soluble in the first phase, a co-solvent, an oil, and water. The first solvent will typically comprise about 75–90% by volume of the first phase. The first polymer is selected to be one soluble in the first phase and typically will comprise about 1–5% by volume of the first phase. A small amount of a co-solvent is also added to the first phase, which co-solvent may also function as a co-surfactant. Oil comprising about 1–10% by volume is also added to the formulation. The first phase will also contain about 1–5% water by volume.

The method next calls for formulating a second phase, immiscible with the first phase. The second phase comprises a second solvent, a second polymer soluble in the second phase, a surface active agent, and a salt. The relative, approximate volume percentages of these constituents is about 70–98% second solvent, 1–10% second polymer, 1–4% surface active agent, and 0–3% salt.

In order to ensure that the liquid-liquid interactions necessary to form the microcapsule will occur, certain of the constituents of each phase are selected relative to one another. Thus, the surface active agent in the second phase is selected such that it will have a hydrophilic/lipophilic balance value greater than that of the first polymer constituent of the first phase. Generally, the most useful surface active agents have been found to be those which are non-ionic and which have a hydrophilic/lipophilic balance value of 10.0 or greater. Next, the second polymer constituent of the second phase is selected to have a hydrophilic/lipophilic balance value lower than that of the surface active agent constituent of the same phase. While not an exhaustive list, certain hydrophilic/lipophilic balance values of materials which may be used in the formulations of the invention are provided below.

Hydrophilic/Lipophilic Balance (HLB)
(McCutcheon 1979)

| Compound | HLB |
| --- | --- |
| Glycerol trioleate | 0.8 |
| Cholesterol | 1.0 |
| Triglyceride of coconut oil | 1.4 |
| Sorbitan trioleate | 1.8 |
| Sorbitan tristearate | 2.1 |
| Glycerol monooleate | 2.7 |
| Mono and di glycerides of fat burning fatty acids | 2.8 |
| Glycerol Monostearate (gms) | 2.8–5.0 (3.8 preferred) |
| Propoxylated ethylene diamine plus ethylene oxide | 3–28 |
| Mono/diglyceride | 3.2 |

-continued

| Compound | HLB |
| --- | --- |
| Glycerol mono coconut | 3.4 |
| Mono/diglyceride | 3.5 |
| Propylene glycol mono fatty acid ester | 3.5 |
| Monoethoxyl lauryl ether | 3.6 |
| Stearyl lactyl acid | 3.8 |
| Hydrogenated cottonseed oil | 3.8 |
| Sodium lauryl sulfate | 4.0 |
| Mono and diglycerides with citric acid or lactylic ester or fatty acid | 4.2–4.6 |
| Ethoxylated fatty amine (2 moles ETO) | 4.5 |
| Diethylene glycol monostearate | 4.7 |
| Sorbitan monopalmitate | 4.7 |
| Diethylene glycol monostearate and oleate | 4.7 |
| Ethoxylated (2) cetyl ether | 5.3 |
| Glycerol Monoricinoleate | 6.4 |
| Glycerol monolaurate | 6.8 |
| Triglycerol mono stearate | 7.0 |
| Polyethylene glycol (400 dioleate) | 7.2 |
| Lanolin sterol | 8.0 |
| Ethoxylated nonyl phenol (CO-420 & CO 850) | 8.0–16.0 |
| Polyethylene glycol (400) distearate | 8.2 |
| Sorbitan monolaurate | 8.6 |
| Ethoxylated sorbitan fatty acid esters and alkyl/aryl alcohol | 9.0 |
| Anhydrous lanolin | 10.0 |
| Polyethylene glycol monostearate | 11.0 |
| Polyethylene glycol 400 | 11.2 |
| Ethoxylated (10) cetyl ether | 12.9 |
| Ethoxylated glycerol monostearate (gms) | 13.1 |
| Sorbitan monostearate | 14.9 |
| Sorbitan monooleate with 20 moles ethylene oxide | 15.0 |
| Ethoxylated (20) oleyl ether | 15.3 |
| Ethoxylated (20) stearyl cetyl ether | 15.8 |
| Ethoxylated castor oil | 18.0 |
| Nonyl phenol polyethylene glycol ether | 18.1 |
| Polyethylene glycol 600 mono laurate | 19.6 |
| Sodium lauryl sulfate | 40 |
| Propylene glycol monostearate | 40 |
| Hydroxylated lanolin sodium oleyl sulfate | 42 |
| Blends of GMS and sorbitan monooleate with 20 mols ethylene oxide | 52 |

The basic method next involves creating an interface between the first and second phases. The creation of the interface is achieved in such a way that minimal shear and mixing occurs between the phases. The two immiscible phases are brought together in such a mechanical manner that the fluid shear properties are controlled to low levels, below about 40 dynes/cm$^2$, and such that the adsorptive surface properties at the immiscible interfaces are not significantly altered. Although the exact mechanisms are not fully understood, the inventors believe that the maintenance of certain surface properties, such as the surface tension, Helmholtz charge distribution (electrical double layer), and partitioning of the surfactant molecules between the immiscible phases must remain substantially intact so that lateral phase separation can occur in a manner which allows simultaneous formation of multiple liquid interfaces (oil/water or water/oil) and which results in microcapsules having alternating spherical shells of hydrophilic and hydrophobic liquid layers. This is believed to be the mechanism for the formation of multi-lamellar vesicles which are formed in a single step. Although this can best be demonstrated under microgravity conditions, wherein buoyant convection is absent and diffusion-driven convection and surface tension differences predominate, this also can be accomplished in unit gravity conditions by balancing the density differences between the two liquid phases or by any other mechanical means which prevents excess fluid shear from significantly altering the normal adsorptive surface properties which are determined by the chemical composition of the formulas and the interfacial phenomena among the solvents, polymers and surfactants. In a preferred embodiment, the creation of the interface will occur by sliding individually separated compartments containing the two phases into register with one another in a manner that substantially limits shear and provides gentle mixing.

In the final step of the basic method of forming the microcapsules, conditions are established in order to substantially limit all mixing between the interfaced liquid phases. In the most preferred environment, the two phases would be allowed to interact at their interface without agitation, stirring, shearing or like force. It is preferred to also limit even those quiescent forces such a gravity-controlled sedimenting, phase separation into stratified layers, shifting, drift and the like. Thus, in certain preferred embodiments, only chiefly diffusion-driven convection, surface tension, and interfacial coacervation is used to spontaneously form microcapsules, as the chemical formulations of the different phases assist in lowering the surface free energy across the interface. It is also at this time that formation of the polymeric outer coating is initiated.

In one embodiment, the two liquids thus formulated are separated into distinct compartments or spaces which spaces are each connected to a central diffusion chamber into which each compartment can deliver its resident liquid loading. The compartments are initially closed to access into the central diffusion chamber so that the first and second liquids are kept apart from one another and not allowed to interact. While it is possible to use any number of devices to achieve this separation, a preferred device is a device like the Materials Dispersion Apparatus (MEPS) described in more detail below. The separation of the two liquids is maintained until both liquids and the device containing them can be placed in an environment in which convective mixing may be minimized, such as in a microgravity environment.

The methods of the invention are slightly different depending upon whether the first solvent is selected to be organic or aqueous. Where an organic solvent is used to formulate the first phase, that organic solvent is selected from the group of organic solvents consisting of ethyl alcohol, methyl alcohol and isopropyl alcohol. Where an organic first solvent is used to formulate the first phase, the first polymer is selected to be one soluble in the organic solvent selected. Such a first polymer may be selected from the group of polymers consisting of glycerol monosterate, glycerol monooleate, glycerol monolaurate, glycerol dioleate, glycerol disterate, cholesterol, stigmasterol, phytosterol, campesterol, and lecithins such as phosphatidyl cholines (e.g., Centrolex-F®).

Where the first solvent is aqueous, a slightly different approach is taken. In those instances, the first polymer is again requisitely soluble in the first aqueous phase and may be selected from the group of polymers consisting of polyvinyl pyrrolidone, polyvinyl alcohols, gelatin, gum tragacanth, carrageenan, Karaya gum, Guar gum, gum arabic, alginates, carboxymethyl cellulose, hydroxypropyl cellulose, carboxypropyl cellulose, and lecithins.

Regardless of the formulation with an aqueous or organic first solvent and polymer, the methods of the invention both use a co-solvent which may be selected from the group of co-solvents consisting of $C_3$–$C_8$ alcohols, tetrahydrofuran, dioxane, acetonitrile, dimethylformamide, dimethylacetamide, and dimethyl sulfoxide. Similarly regardless of the organic/aqueous nature of the first solvent and polymer used, the methods of the invention add to the formulation of the first phase an oil. These oils may be selected from the group of oils consisting of unsaturated oils such as poppy seed oil, olive oil, peanut oil, sesame oil, cotton seed oil, soybean oil, safflower oil, corn oil, sunflower seed oil and canola oil or saturated oils such as mineral oil, long chain paraffinic oil, and liquid petrolatum. In a preferred embodiment, poppy seed oil will be iodinated to form iodinated poppy seed oil (IPO) and incorporated into a microcapsule as a marker or tracer for tracking the presence of the microcapsule once injected via radiocontrast detection methods known well to those of skill in the art of radiography.

Whether the method involves an organic or an aqueous first solvent, the second polymer, the surface active agent and the salt may each be selected from a particular group of such compounds. The second polymer may be selected from the group of polymers consisting of polyethyleneglycol 1000–8000 daltons, dextran 1000–10000 daltons, polyvinylpyrrolidone, polyvinyl alcohols, gelatin, gum tragacanth, carrageenan, Karaya gum, Guar gum, gum arabic, alginates, carboxymethyl cellulose, hydroxypropyl cellulose, carboxypropyl cellulose, and lecithins. The surface active agent is selected from the group of surface active agents consisting of sorbitan monooleate treated with ethylene oxide, dextran, polyethylene glycol, $C_{12}$–$C_{20}$ fatty acids, 2-amino-2-methyl-1-propyl aminomethyl propanol amphoteric salts and quaternary ammonium salts. The salt is selected from the group of salts consisting of NaCl, KCl, $CaCl_2$, $MgCl_2$, quaternary ammonium salts such as, cetyl trimethylammonium bromide and 4-methoxy-4(3-phosphatidyl choline)spiro(1,2-dioxetane-3-g,1-adamantane) disodium salt.

In certain embodiments of the methods of the invention, pharmaceutical compositions will be incorporated into the microcapsule. Where such pharmaceuticals are thusly incorporated, they may be introduced initially as a solute or as particulates suspended in one or the other of the liquids used to formulate the layers of the microcapsules. In certain embodiments, the pharmaceutical is introduced in one of the phases or layers used to produce the microcapsule at a concentration sufficient to allow nascent crystal formation within said microcapsule. Crystal formation may occur at or near the time of formation of the microcapsule containing the dissolved pharmaceutical material. The aqueous solvent system used to dissolve an aqueous-soluble pharmaceutical is selected to permit water molecules to migrate away from the drug-containing layer into the alcoholic mixture. The process of crystal formation is likely to be promoted in this manner after formation of the microcapsule. In fact, it is possible to enhance the crystallization process after the microcapsule is formed by controlled transport of the solvent phase or layer in which the pharmaceutical to be crystallized is a solute. In certain embodiments, the crystal thus formed may take up most of the internal capacity of the microcapsule.

Multi-layered microcapsules, with both hydrophobic and hydrophilic drug compartments, as produced by the methods of the invention enable diffusion of complimentary drugs from the same microcapsule, e.g. antibiotics and immunostimulants to treat resistant infections or multiple fibrinolytic drugs to dissolve emboli. Co-encapsulation of radio-contrast medium as provided herein enables oncologists to monitor the delivery of anti-tumor microcapsules to target tumors using computerized tomography and radiography that track the distribution of microcapsules after release from the intra-arterial catheter. Such microcapsules will have important applications in chemotherapy of certain liver, kidney, brain and other tumors.

The diameters of microcapsules possible to attain using the methods of the invention are also of particular usefulness in medical applications. Thus, whereas prior art methods have been able to routinely produce microcapsules over 1–10 micron average sizes, the present invention's methods provide similarly-sized microcapsules of 1–20 micron diameters for intravenous administration. Also provided are 25–300 micron sized microcapsules particularly useful in interarterial chemoembolization of tumors, and microcapsules in the range of 300 micron and greater (up to 500 microns, for example) diameters useful in interperitoneal or intramuscular administered drugs.

The pharmaceutical composition encapsulated in the microcapsule may be one soluble in aqueous solutions or may be one soluble in organic solutions. This, of course, governs the selection of the phase or layer in which the pharmaceutical composition is formulated. The microcapsules of the invention and methods for producing them are of particular utility when formulating organic-soluble drugs as these type of drugs are otherwise very difficult to administer. The pharmaceuticals may be those selected from the group of such widely diversified pharmaceutical compositions as that consisting of cytotoxins, proteases, cytokines, anti-nauseants, steroids, anti-fungal agents, fibrinolytic enzymes, and antibiotics. The inventors have successfully encapsulated representatives of these classes of pharmaceuticals using the methods of the invention. It is also possible to incorporate a pharmaceutical composition which is not initially dissolved in one or another of the phases or layers, but rather which drug is in suspension. As noted above, depending upon its solubility and upon where the pharmaceutical chemist wishes to locate the drug, it is possible to formulate a drug in any of the phases or layers, by dissolving or suspending the drug as needed.

The methods of the invention surprisingly demonstrated the ability to package very high concentrations of drugs in the layers formed. It is possible, using the methods of the invention, to formulate a pharmaceutical at a concentration sufficient to allow nascent crystal formation within the microcapsule once it is formed. These microcapsules, due in one regard to their being constructed with outer polymeric coatings, are also particularly flexible yet rugged (able to withstand shear forces greater than 10 dynes/cm$^2$). As will be related specifically below, microgravity experiments, on sounding rockets (1989–92) and Shuttle missions STS-52 (1992) and STS-56 (1993) using an automated Materials Dispersion Apparatus, produced multi-lamellar microcapsules containing both Cis-platinum (anti-tumor drug) and iodinated poppy seed oil (a non-radioactive, radiocontrast medium), surrounded by a polymeric skin. Microcapsules formed with amoxicillin (antibiotic) or urokinase (a clot dissolving enzyme), co-encapsulated with IPO, were still intact after two years after return to 1-g environments. In many instances, microcapsules were formed with the Cis-Platinum or amoxicillin so concentrated that crystals of the drugs formed inside.

Surprisingly, the methods of the invention have demonstrated a unique ability to encapsulate such saturated drug solutions, and since the overall partitioning characteristics between immiscible layers facilitates solvent transport out of the aqueous layer, it is possible to concentrate the drug to the point that formation of drug crystals occurs within the microcapsules. This ability of the microcapsules and methods of the invention provides the maximum drug payload per microcapsule and the best drug release kinetics for prolonged treatment at maximum drug diffusion rates.

Microcapsules containing a large volume component of crystalline drug provide the most concentrated drug possible when it is released at the target site. Until the crystals are completely dissolved, the drug release rate is independent of time (zero order release kinetics). When the crystals have dissolved, the drug release rates revert to first order kinetics (exponential with time). The encapsulated crystals of the invention are in the range of 1–50 microns in diameter. Since these crystals are precipitated in situ, they are quite different from the other commercially-available crystalline drug delivery systems (e.g., Microcrystal®) which use phospholipids to encapsulate tiny particles or crystals of drugs with an average diameter of only 0.3–1.0 micron [Parikl and Stern 1994].

Another surprising aspect of the microcapsules described herein is their ability to form crystals within the microcapsule. The inventors have observed that a protein contained in one of the immiscible layers within a microcapsule will form large, well structured crystals upon irradiation of the microcapsule with an energy source such as uv light that results in vigorous mixing within the microcapsule. The crystals have been observed to form within seconds during irradiation.

It is also possible to additionally treat the microcapsules thus formed with additional steps. In some instances, the methods of the invention, regardless of whether they initially use an organic or an aqueous first solvent, formulate a third phase comprising an oil or $C_{20}$–$C_{38}$ paraffin and, contact the formed microcapsule with the third phase. In other instances, the methods of the invention form a two-layered microcapsule, then formulate a third phase comprising an aqueous solution and, contact the formed microcapsule with the third phase. The basic method and alternatives are summarized below.

|  |  | Group 1 | Group 2 |
|---|---|---|---|
| Solution 1 | | Solvent 1 is a hydrocarbon | Solvent 1 is aqueous |
| | | Polymers are hydrocarbon soluble, selected to form the outer coating (typically of lower HLB values) | Polymers (skin) are water soluble, but can be extended into organic phase (includes phospholipids) Ex. Centrolex F□ |
| | | Co-solvents alcohols, hydrocarbons (act as co-surfactants) | Co-solvents same, but often less % |
| | | Oils saturated or unsaturated oils | Oils same |
| | | Pro-drug or activator dissolved (or suspended particulate) | Pro-drug or activator dissolved (or particulate) |
| Solution 2 | | Solvent 2 aqueous | Solvent 2 same |
| | | Polymers water soluble (PEG, Dextran) | Polymers same |
| | | Surfactants (typically higher HLB value) | Surfactants same but often less % |

-continued

|  | Group 1 | Group 2 |
|---|---|---|
| | Salts ionic, quaternary ammonium salts | Salts same, but often different % |
| | Pro-drug or activator | Pro-drug or activator |
| Solution 3 | Oils hydrocarbons | Oils same |
| | Polymers hydrocarbon-soluble | Polymers same |
| | Drugs can be included | Drugs can be included |
| | -- OR -- | --- OR -- |
| | Alternative aqueous solution | Alternative aqueous solution |
| | coating-adjuvants | coating same |
| | lins | polymer same |
| | polymers - aqueous soluble | surfactants same |
| | surfactants - | |

As can be seen in light of the present disclosure, the prodrug may be added to the Group 1 solutions and the activator to the Group 2 solutions as is appropriate to the solubility of the prodrug and activator.

Traditional emulsion methods form a O/W/O (oil/water/oil) or W/O/W (water/oil/water) liquid system which is designed to retain the internal phase(s) within the external solvent unless the emulsion is broken, whereupon the liquid phases separate. In the methods of the invention, the use of surfactants and co-surfactants permits formation of an emulsion of large spheroids (not small microspheroids) of one phase dispersed in the other phase configured in a sphere. The sphere is also surrounded by another immiscible liquid layer (opposite phase to that of the innermost liquid sphere) and then (often) this multi-layered sphere is contained in another opposite-phase liquid layer and finally the entire multi-layered sphere is contained in an outer skin. The results of the process of the invention are not to form a traditional O/W/O or W/O/W emulsion (which is a fine dispersion of one phase in another), but rather to form multi-lamellar, alternating immiscible-layer microcapsules contained within a thin, semi-permeable outer skin. In the microcapsules of the invention, the immiscible phases are distinct and separated according to the surface tension characteristics of the liquids at each interface.

Thus, in certain embodiments of the methods and compositions of the invention, the multi-layered microcapsule will be produced which comprises at least three alternating layers or phases. Thus, if the first layer is an aqueous layer or core, the next layer may be an organic layer. This organic layer may then be covered over by a second aqueous layer which forms on its outer surface a polymeric skin. Conversely, the liquid at the core of the microcapsule may be an organic liquid layered over by an aqueous layer followed by another organic layer which forms a polymeric skin over the surface of the microcapsule. Certainly, extension of these basic formulations may be envisioned where four or more layers are possible or where multiple skins or coatings are utilized.

Whether used in conjunction with a two-layer microcapsule or with microcapsules with more than two layers, the coatings of the present invention are of substantial utility, particularly when the methods are carried out at Earth-normal gravity. The coatings can be either substantially of a hydrophobic nature or of a hydrophilic nature as described below and are derived from addition of certain polymers in the initial formulations of the liquids used to make the microcapsules. Where hydrophobic coatings are used in conjunction with drug-delivery systems, the coatings are selected for their complementary permeability to the drug to be delivered. The polymers are also selected for their flexible characteristics after formation and curing which is of particular utility during intravascular transport and allows higher packing densities for forming emboli such as in chemoembolization therapy. Thus, for example where a water-soluble drug is to be delivered, the drug is contained in an inner aqueous layer over which is placed a coating permeable to the dissolved drug. In alternate embodiments, the drug may be more hydrophobic and will be contained in a hydrocarbon layer within the microcapsule. In either embodiment, the drug may actually be a prodrug, and an activator may be contained in a layer immiscible with the layer containing the prodrug. Preferably, the coating material should be impermeable to solvents or oils. The coatings which have been observed to be deposited on the surfaces of the microcapsules of the invention are about 0.01–2.0 microns thick where the coating is a hydrophobic coating, and about 0.1–5.0 microns thick where hydrophilic coatings are deposited.

The additional steps and third formulated phases may also be used advantageously to provide the microcapsule with specific characteristics. Thus, the third phase may further comprise a pharmaceutical composition which is added to the formed surface of the microcapsule. The third phase may also be used to add a pharmaceutical composition such as an adjuvant. The adjuvant may further comprise an immunoglobulin, other protein, hydrocolloid or polysaccharide. This is of particular utility in designing microcapsules with unique immunologic, proteinaceous, surface charge, or other surface characteristics which makes them selectively adhere to certain target tissues (cells) or renders the microcapsules attractive to certain phagocytic cells (when the cells are the actual target for the therapeutic drug). Where the adjuvant is a hydrocolloid, it may be selected from the group of such hydrocolloids consisting of collagen, isoelectric gelatin, agar, gum arabic, gum tragacanth, alginates, cellulose derivatives, guar gum, cyclodextrins, and carrageenans. The third phase may also further comprise a surface active agent.

The third aqueous phase can also contain a chemical activator which acts upon the inactive form of the pharmaceutical agent (drug) as it diffuses out of the inner layers of the microcapsule. The function of the activator is to chemically convert the inactive drug to its active form just before it is released from the microcapsule. This is illustrated when the pharmaceutical is a pro-enzyme and where the activator is another proteolytic enzyme which cleaves the pro-enzyme at active site to render the molecule biologically active. This embodiment can be used to deliver very labile drugs which have limited shelf-lives or short biological half-lives whereupon the activator (third phase) can be added just prior to intravascular administration such that the inactive drug becomes activated after the microcapsules have reached the target site. This can maximize the therapeutic effectiveness of the short-lived drug at the target site of action.

One or more of the phases of the microcapsule of the invention may further comprise fluorescent molecules selected from the group of fluorescent molecules consisting of fluoresceins, cyanins, naturally fluorescent molecules, rhodamines, and others excited between 260 and 700 nanometers. This is particularly useful where radiocontrast media are not desirable or where an additional tracking method is useful or where it is of value to monitor the presence or absence of a layer in the microcapsule, fluorescent molecules may be incorporated into the microcapsule of the invention. Thus, for instance, as described more fully below, it may be useful to incorporate a hydrophilic fluorescent molecule in the aqueous liquid in order to determine the relative location and number of aqueous liquid layers in a certain production batch of microcapsules produced by the methods of the invention.

Critical to the success of the methods of the invention is the substantial limitation of mixing between said phases to diffusion-driven convection and low fluid shear (less than 50 dynes/cm$^2$). One manner in which to so limit other types of mixing is to carry out the methods under microgravity. Microgravity is defined as a gravity force of less than $1 \times 10^{-3}$-g. Such gravitational environments may be achieved in a variety of ways, at least some of which are detailed herein. For instance, microgravity may be achieved in certain trajectories of sounding rockets. Even longer periods of microgravity may be obtained with temporary orbiters such as the space shuttle. Relatively indefinite periods of microgravity may be obtained in permanent or semipermanent orbital space craft such as the orbital space station and other geosynchronous orbital satellites. The exposure of the first and second liquids to microgravity has been found to be effective in forming the microcapsules of the invention where the exposure is at least 6.5 minutes in duration. Certainly, as described more fully below, greater exposure periods have also been proven successful. The inventors have shown that periods of exposure as short as a few seconds will also produce adequate numbers of microcapsules.

In formation of microcapsules, however, the methods of the invention will not necessarily use microgravity in order to limit mixing between the phases. Of course, such limitations of mixing can be promoted by carrying out the methods below ambient temperature. Limitation of interactions between the phases is best promoted by substantially balancing the specific gravity between said phases as is described below. The formulations and methods necessary to achieve Earth-normal microcapsule formation are described in greater detail herein. In either case, or in combinations of these techniques, mixing between the two phases may be chiefly the result of diffusion-driven convection.

The inventors have found that there is a greater size distribution which results from microencapsulation at Earth-normal gravity. At least a partial reason for this wider size distribution is apparently the inability under Earth-normal gravity to avoid certain sedimentation phenomena alone and sedimentation effects combined with weight-related contact of sedimented microcapsules. These facts require some additional manipulation under Earth-normal environments not required in the 0-g environments—namely, sieving of the resulting microcapsules in order to generate more uniform fractions. Therefore, at Earth-normal gravity, the utility of the outer coating of the microcapsules of the present invention become even more important. Enhancing the ruggedness of the Earth-normal microcapsules by curing and other steps as related herein may also be used.

A preferred method of making a multi-layered microcapsule comprises: formulating a first phase comprising an organic solvent selected from the group of organic solvents consisting of ethyl alcohol, methyl alcohol and isopropyl alcohol, a first polymer soluble in the first phase selected from the group of polymers consisting of glycerol monosterate, glycerol monooleate, glycerol monolaurate, glycerol dioleate, glycerol disterate, cholesterol, stigmasterol, phytosterol, campesterol, lecithins such as phosphatidyl cholines (e.g., Centrolex-F®), a co-solvent selected from the group of co-solvents consisting of $C_3$–$C_8$ alcohols, tetrahydrofuran, dioxane, acetonitrile, dimethylformamide, dimethylacetamide, and dimethyl sulfoxide, an oil selected from the group of oils consisting of poppy seed oil, olive oil, peanut oil, sesame oil, cotton seed oil, soybean oil, safflower oil, corn oil, sunflower seed oil, canola oil (unsaturated oils), or mineral oil, long chain paraffinic oil, and liquid petrolatum (saturated oils), and water; formulating a second phase immiscible with the first phase, the second phase comprising water, a second polymer soluble in the second phase selected from the group of polymers consisting of polyethyleneglycol 1000–8000 daltons, dextran 1000–10000 daltons, polyvinylpyrrolidone, polyvinyl alcohols, gelatin, gum tragacanth, carrageenan, Karaya gum, Guar gum, gum arabic, alginates, carboxymethyl cellulose, hydroxypropyl cellulose, hydroxyethyl cellulose, carboxypropyl cellulose, lecithins, a surface active agent selected from the group consisting of sorbitan monooleate treated with ethylene oxide, dextran, polyethylene glycol, $C_{12}$–$C_{20}$ fatty acids, cyclodextrins, PEG-dextran copolymer, PEG-acrylates, lactides, galactides, chitosan, Zein®, carbapol®, polyoxamers, quaternary ammonium salts, and a salt selected from the group of salts consisting of NaCl, KCl, $CaCl_2$, $MgCl_2$, quaternary ammonium salts, cetyl trimethylammonium bromide, 2-amino-2-methyl-1-propyl aminomethyl propanol, and 4-methoxy-4 (3-phosphatidyl choline)spiro(1,2-dioxetane-3-g,1-adamantane) disodium salt; the surface active agent having a hydrophilic/lipophilic balance value greater than that of the first polymer; the second polymer having a hydrophilic/lipophilic balance value lower than that of the surface active agent; creating an interface between the first and second phases in a manner that substantially limits fluid shear, and, substantially maintaining adsorptive surface characteristics of said interface.

Microcapsule products produced by any of the methods of the invention are also claimed. The methods of the invention are used to form unique multi-lamellar, microcapsules, having alternating hydrophilic and hydrophobic liquid layers surrounded by a flexible, semi-permeable, polymeric outer "skin". The outer skin which can be either hydrophilic or hydrophobic, is designed to allow controlled drug diffusion out of the microcapsule.

Unlike any natural phospholipid or other component of cell membranes, the outer skin of the microcapsules of the invention avoids recognition and phagocytosis by immune cells, thereby increasing the amount of drug delivered to the tissues. The multi-layered microcapsules of the invention can entrap multiple drugs in different solvent compartments and saturated solutions of drugs which may then form crystals inside the microcapsule. Radiocontrast medium can be co-encapsulated with drugs in the same microcapsule. A magnetic resonance contrast agent can also be encapsulated such as various metallo-organic compounds including aqueous soluble ferrous gluconate, Gadolinium diethylene triamine pentaacetic acid and hydrocarbon-soluble, iron pentacarbonyl.

The microcapsules of the invention have been found to provide a surprisingly uniform distribution of diameters. This uniformity is particularly important in its medical applications. The microcapsules thus produced can be used to deliver several drugs which can be released sequentially to the target tissues. The deformable, liquid-filled microcapsules also have advantages over solid matrix microcapsules in achieving maximum packing density in blood vessels, thereby decreasing blood flow to target tissues. This enhances the therapeutic effect of combined drug delivery and reducing the blood supply to vascular tumors (chemoembolization).

The methods of the invention result in more spherical, uniform size distributions of microcapsules. When comparing certain prior art equipment and methods for forming microcapsules (Microfluidics, Inc.,), the inventors found that even the preferred formulations of the invention were incapable of providing such uniformity. In certain instances, hardly any microcapsules formed at all where mixing and vortexing were used to distribute one phase into the next. In others, poorly formed and non-spherical microcapsules resulted. In contrast to the failures of the prior art methods, the methods of the invention were successfully used to generate uniform, spherical microcapsules both under unit gravity and under microgravity conditions. Such uniformity enables superior drug delivery. Enhanced uniformity also enables better dose distribution calculations for establishing the therapeutic dose in the treatment of specific diseases, especially treatment of certain types of tumors. Importantly, the methods of the invention allow the formation of larger-sized, multi-lamellar microcapsules (1–500 micron) than heretofore possible. Such a capability allows multilamellar microcapsules to be made specifically for inhalation and deposition in the lungs. This uniformity allows facile sieving or filtering of the microcapsule products in order to obtain highly uniform diameter fractions.

As previously noted, the microcapsules of the invention may contain polysaccharides. Inclusion of such polysaccharides is one of several aspects of the methods of the invention that enhance the formation of the microcapsules. The inclusion of injectable polysaccharides in the formulations of the invention contributes to the driving forces that control phase separation and phase partitioning of the entrapped drugs. The polysaccharides also provide increased shelf-life and stability of the parenteral suspensions. Use of the neutral salt solutions in the aqueous phase enhances micelle formation, lateral phase separation, and increases the dispersion of microcapsules and their stability as they are formed. In certain embodiments, phosphate buffered saline containing dextran may be used.

The methods of the invention in a preferred embodiment utilize a non-phospholipid outer coating. The microcapsules formed by this method are contained in a thin, semi-permeable, outer membrane comprised of hydrophobic (e.g. mono- or polyglycerides or waxy-polymers) or hydrophilic polymers (e.g., PVA or PVP), depending on the desired diffusion release rate of the encapsulated drug. Thus, the coating has the advantage of allowing design of the appropriate drug diffusion and release characteristics while avoiding certain of the disadvantages of conventional liposomes (and lipid bilayers). In particular, the coating produced by the methods of the invention around the outer surface of the microcapsule avoids being readily detected and largely eliminated by the reticuloendothelial system (RES). The outer skin protects the microcapsules against shear forces encountered during manufacturing processes and during transport within the vascular system en route to the target tissues. The hydrophobic outer membrane also can be designed to retard oxygen transport, thereby reducing oxidative degradation of the entrapped drug and improving the shelf-life of the parenteral suspensions. The flexible/deformable outer skin on the microcapsules of the invention results in increased packing densities within vascular beds. This results in microcapsules superior to solid microspheres (e.g. gelatin, albumin or starch) commonly used for chemoembolization therapy against tumors. The formulations used to produce the microcapsules of the invention are summarized below.

| | Formulas for Primary, Secondary and Tertiary Solutions for Microencapsulation | | |
|---|---|---|---|
| | Primary Solution (also can contain drug) | Secondary Solution | Tertiary Solution (also can contain dissolved drug) |
| Group 1 | First Solvent (75–90%) ethyl alcohol methyl alcohol isopropyl alcohol | Second Solvent water (70–98%) | Oils (up to 100%) IPO Heavy mineral oil olive oil same as in primary soln. Paraffins ($C_{20}$—$C_{38}$) |
| | Organic Co-solvent 0–20% $C_4$—$C_8$ alcohols tetrahydrofuran (THF) dioxane acetonitrile dimethylformamide F) dimethyl sulfoxide SO) | Polymers (1–10%) polyethylene glycol PEG - 1000–8000 | Alternative Aqueous solutions containing - Immunoglobulins Albumin Gelatin Hydrocolloids plant sterols phospholipids polysaccharides - starches - cyclodextrins |

-continued

Formulas for Primary, Secondary and Tertiary Solutions for Microencapsulation

| | Primary Solution (also can contain drug) | Secondary Solution | Tertiary Solution (also can contain dissolved drug) |
|---|---|---|---|
| | Polymers (1-5%) (monoglycerated) glycerol monostearate glycerol monooleate glycerol monolaurate (polyglycerides) glycerol dioleate glycerol distearate | (polysaccharides) Dextran 4000–20000 (range 10000–100000)) others polyvinyl-pyrrolidone polyvinyl | Polymers |
| | (sterols) cholesterol piant sterols - stigmasterol phytosterol campesterol | Surfactants (ionic and non-ionic) (1–4%) sorbitan monooleate plus ethylene oxides Dextran PEG $C_{12}$—$C_{20}$ fatty acid quaternary $NH_4$ salt | Surfactants (1–4%) (ionic and non-ionic) long chain celluloses |
| | (phospholipids) lecithins e.g., phosphatidyl choline (Centrolex-F□) Water (1–5%) water | Additional Polymers (1–10%) (hydrocolloids) gelatin gum tragacanth carrageenans karaya gum guar gum alginates | Additional Polymers Same as secondary solution |
| | Oils (unsaturated or saturated) (1–10%) iodinated poppy seed oil) mineral oil cotton seed oil olive oil safflower oil canola oil peanut oil sesame oil corn oil | (celluloses) celluloses (CMC, WEC, HPC) Salts (0–3%) NaCl KCl, $CaCl_2$, quaternary $NH_4$ salts, cetyl P, PPD | |
| | Dissolved Drugs (1% to saturation) therapeutic of choice | Dissolved Drugs (1% to saturation) soluble therapeutic | Dissolved Drugs (1% to saturation) |
| Group 2 | Aqueous First Solvent water (70–90%) | Same as Group 1 | Oils (up to 100%) Same as Group 1 |
| | Co-solvents (0–20%) $C_3$—$C_8$ alcohols tetrahydrofuran (THF) dioxane acetonitrile dimethylformamide F) dimethyl sulfoxide SO) | Co-Solvents Same as primary solution | Alternatives Aqueous solutions Same as Group 1 |
| | Polymers hydrophilic (water soluble) polyvinylpyrrolidone P) polyvinyl alcohols (PVA) hydrocolloids gelatin gum tragacanth carrageenans karaya gum guar gum | Polymers (1–10%) Same as Group 1 Surfactants (1–20%) (ionic and non-ionic) Same as Group 1 | Polymers Same as Secondary Solution Surfactants Same as Secondary |

-continued

Formulas for Primary, Secondary and Tertiary Solutions for Microencapsulation

| Primary Solution (also can contain drug) | Secondary Solution | Tertiary Solution (also can contain dissolved drug) |
|---|---|---|
| alginates | | Solution |
| celluloses CMC, CPC | Additional Polymers | |
| phospholipids | 1–10% | |
| lecithins | | |
| phosphatidyl choline | | |
| Centrolex F | | |
| polysaccharides | Salts (0–3%) | |
| corn starch | Same as Group 1 | |
| cyclodextrins | | |
| Oils (unsaturated or saturated) 1–10% | | |
| iodinated poppy seed oil (IPO) | | |
| mineral oil | | |
| cotton seed oil | | |
| olive oil | | |
| safflower oil | | |
| canola oil | | |
| peanut oil | | |
| sesame oil | | |
| corn oil | | |
| Dissolved Drugs 1% to saturation | Dissolved Drugs 1% to saturation | Dissolved Drugs 1% to saturation |

Where the microcapsules of the invention comprise a pharmaceutical composition, certain medically related advantages may be obtained. Thus, due to the uniformity and ease with which the methods of the invention allow formation of multilamellar microcapsules, co-encapsulation of multiple drugs is made possible. Thus, for instance, as will be described more fully below, co-encapsulation of drugs and radiocontrast medium in the same microcapsules is made possible by the methods of the invention. Such co-encapsulation allows radiological monitoring of the tissue distribution during intravascular delivery. Additionally, incorporation of fluorescent-labels for entrapped drugs enables accurate measure of the drug compartment volumes (using fluorescent imaging techniques) and convenient determinations of the drug loading efficiencies, particle size distributions and measurement of shelf-life stability of the final parenteral suspensions. In some applications made possible by the methods and compositions of the invention, the organic phase can include a tracer compound or radiocontrast medium to provide the additional advantage of real-time imaging of the microcapsules with computerized tomography (CT) scanning as they are released from the catheter en route to the target tissue. Other examples include aqueous soluble metallo-organic compounds used for diagnostic imaging such as ferrous gluconate or Gadolinium diethylene triamine pentaacetic acid (Gd-DTPA) used for nuclear magnetic resonance imaging and hydrocarbon soluble agents such as iron pentacarbonyl which also may be used for NMR imaging.

Production of multi-layered microcapsules via the methods of the invention which possess alternating hydrophobic and hydrophilic drug compartments allows for design of multiple-therapy microcapsules. Spontaneous formation of microcapsules with one or more large hydrophobic solvent compartments increases the potential application for delivery of more aqueous-insoluble drug at target sites with adequate vascular networks. By using the microcapsules made possible by the methods of the invention, sequential diffusion of two or more drugs out of the same microcapsule may be achieved at the target tissues. The incorporation of aqueous-soluble cyclodextrin which can act as an internal hydrophobic drug carrier is also made practical using the single step methods and formulations provided in this invention. This extends the capability of the invention in delivering otherwise aqueous-insoluble drugs.

For instance, the use of multiple drugs within the same microcapsule provides microcapsules specifically designed for chemoembolization treatments. Multiple-drug microcapsules also may be used to deliver first a chemotherapeutic drug which kills tumor cells, and then an immuno-adjuvant (tumor necrosis factor) or immunological stimulant (e.g. interferon-g) that would enhance the patient's immune response to the tumor. Multiple-drug microcapsules can also be used to deliver combinations of chemotherapeutic drugs to tumors that are located in privileged sites, such as brain tumors. For example, and as described more fully in the examples to follow, simultaneous delivery of different types of drugs in the same microcapsule is made possible with the methods and compositions of the invention, e.g. diaziquone and cis-platinum to brain tumors via the carotid artery [Kimier et al. 1993]. Multi-layered microcapsules may also be used to treat deep infections that are resistant to systemic antibiotics. In these applications, one or more antibiotics may be sequentially delivered to the site of the infection. Multi-layered microcapsules can be designed to protect active forms of urokinase and other thrombolytic enzymes until they are delivered and entrapped at the local site of a blood clot, where therapeutic doses of the enzyme may then diffuse out to dissolve the unwanted embolism. The multi-lamellar microcapsules can also be used to deliver immunostimulants; cytokines such as Interferons, Interleukins, and growth factors; antinauseants such as metoclopramide and tetrahydrocannabinol; multiple fibrinolytic enzymes such as urokinase (uPA), tissue plasminogen activator (tPA)

and streptokinase; steroids such as hydrocortisone, dexamethasone, etc.; anti-fungals such as nystatin and griseofulvin, anti-virals such as amantidine, iododeoxuridine, riboviran; and multiple antibiotics such as amoxicillin, ampicillin, etc.

As used herein the term contain or contained in a microcapsule or in a liquid phase or layer is construed to have its normal meaning, and may include suspended or dissolved as in a liquid layer, or interface, and also includes the meaning associated with a liquid layer or polymer shell including on its inner or outer surfaces. The terms contained or associated with a liquid layer or phase may also be interpreted to mean having a higher solubility in that phase, than in another phase within the microcapsule, or preferentially partitioning in a particular phase or in the interface. As used herein, the term "prodrug" or "proenzyme" includes the meaning of a precursor, such as intraglandular prohormones, or the meaning of an agent whose drug or enzymatic activity, or pharmacological action, results from a conversion or transformation into an active form. Such conversion may be the result of a metabolic process or biotransformation, or it may be the result of a manmade reaction.

BRIEF DESCRIPTION OF THE DRAWINGS

For a detailed description of a preferred embodiment of the invention, reference will now be made to the accompanying drawings wherein.

DETAILED DESCRIPTION OF THE PREFERRED EMBODIMENTS

Figure 1:
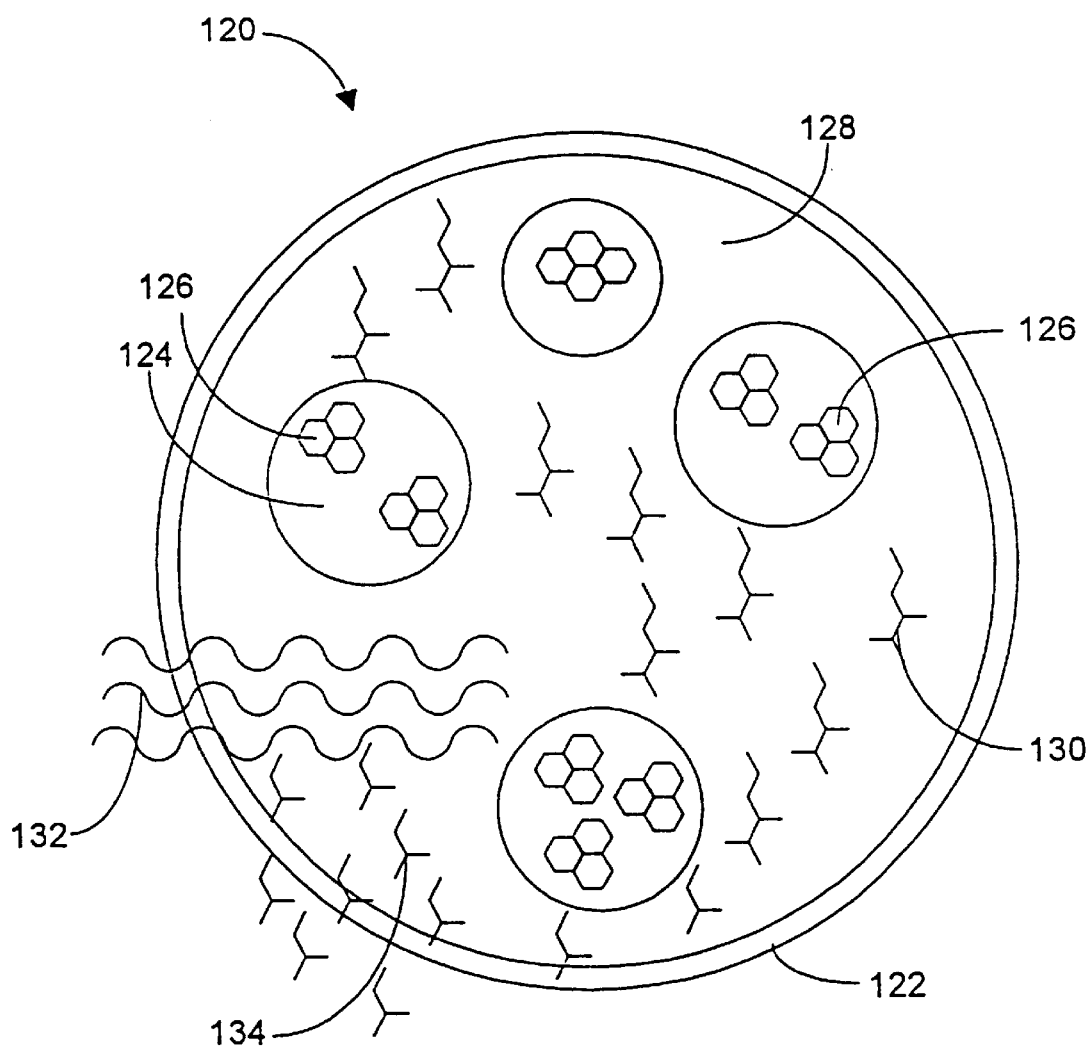
FIG. 1. Schematic of in situ activated microcapsules.

The present disclosure provides methods of encapsulating multiple drugs or biological therapeutics into liquid microcapsules or liposomes that are designed for delivery to selected tissues or organs where, upon activation, a short-lived drug can be released directly to the target area by diffusion out of the microcapsules. A method of the present disclosure may be used to form multi-lamellar microcapsules having alternating hydrophilic and hydrophobic liquid layers surrounded by a flexible, semi-permeable, polymeric outer "skin." In this embodiment, the outer skin is designed to allow sustained diffusion of the bioactive drug from the microcapsule.

The methods and compositions of the present invention may use special formulations of solubilized drugs, surfactants, polymeric co-surfactants, and energy absorbing components within a specific immiscible liquid phase. The energy absorbing medium (e.g. photo activator, thermoabsorber, etc.) absorbs electromagnetic, ultraviolet (UV), infrared (IR), ultrasonic, radiofrequency (RF), or microwave radiation and thereby causes chemical activation of a chemical substrate or drug precursor into a bioactive drug molecule which can readily diffuse out of the microcapsule. The absorbed energy also can be used to create thermal convection, Maragoni flows or other high velocity flows that can cause interfacial mixing, redistribution of partitioning compartments within immiscible phases, and increased radiocontrast of selected components within certain liquid compartments. This is exemplified by UV (220–390 nanometers) photoactivation of microcapsules containing drugs, fluorescent compounds and radiocontrast media in the same microcapsule. The in situ activated microcapsules are characterized by: outer polymeric membranes that are both transparent to the activating radiations and are permeable to the bioactive drug thereby allowing sustained time-release of the active drug; immiscible fluid compartments inside the microcapsules or internal spheroids surrounded by thermosensitive or a shear sensitive interfacial boundary or membrane, containing chemical components that absorb the activating energy; chemical reactions or convective mixing that convert the prodrug or proenzyme to the bioactive form or change the molecular form of a drug (which is already bioactive) to increase its diffusion rate out of the microcapsule or its bioavailability once it has been released; and a longer shelf-life than that of the bioactive drug dissolved or suspended in the carrier solution.

Included within the present disclosure are multi-layered liquid microcapsules and methods of forming the multi-layered liquid microcapsules comprising a drug permeable outer skin or membrane surrounding a sphere of immiscible fluid compartments. The immiscible compartments may contain a drug precursor in one phase and an activating agent in another phase. The activating agent may be activated by exposure to external electromagnetic radiation or other forms of activating energy causing it to react with the drug precursor to produce an active drug or agent.

Also included are methods of storing pharmaceuticals or bioactive drugs by producing the microcapsules as described in the previous paragraph and storing such formulations so that they are protected from light and other forms of activating energy until they are to be administered to a subject.

Embodiments of the present invention include methods of exposing the microcapsules to activating radiation or other forms of activating energy. These methods include, but are not limited to the following:

(a) Direct exposure of the microcapsules in dry or liquid dispersion just prior to dispensing. This method may be accomplished, for example, by exposure to radiation from a band pass filter system, laser light infrared light, radio waves or microwaves, or a combination of same, all of which are transmitted through the outer membrane of the microcapsules to be absorbed by the activating agent which has been co-encapsulated with the precursor drug.

(b) Entrapment of the microcapsules in tissue followed by external administration of the activating energy through the skin and outer tissues of a subject without physiological damage and absorption of the energy by the activating agent within the microcapsules.

(c) Entrapment of microcapsules in arterioles, venules, or tissues, followed by exposure of the microcapsules via intravascular catheters, or other internal devices containing a fiber optic probe, electromagnetic transducer, or other miniature energy transducer that can transmit the activating energy locally to the entrapped microcapsules.

In the practice of certain embodiments of the inventions, the absorption of the activating energy may result in a chemical reaction between an activator and a prodrug or enzyme precursor that produces a bioactive molecular moiety, or such absorption may drive fluid mixing and turbulent fluid flows wherein the internal mixing of the immiscible internal phase containing the prodrug and the internal phase containing the activator results in production of the bioactive form of the drug. Alternatively, absorption of activating energy may occur inside inner spheroids surrounded by a thermosensitive membrane containing a solution of the activating agent where energy deposition increases the temperature in the spheroid causing the thermosensitive membrane to rupture or dissolve, allowing the activating solution to mix with the next outer solution containing the prodrug or substrate to produce the active agent which then diffuses out of the microcapsule. The activating energy may also be absorbed by the outer membrane of the microcapsules, or by an activating agent that, upon activation, dissolves or disrupts the outer membrane thereby releasing a bolus of bioactive drug at the local site.

An embodiment of the present invention is also microcapsules in which activating energy is absorbed by radio-contrast media contained in the microcapsules, thus increasing the radio-opacity of the media while the microcapsules are trapped in tissue. Examples of such radiocontrast media include, but are not limited to halogenated oils such as halogenated poppy seed oil, cotton seed oil, soybean oil, safflower oil, corn oil, sesame seed oil, canola oil, and others that can be readily iodinated to produce a radio-opaque contrast medium for radiographic imaging.

For the purposes of this disclosure, the terms "a", "an" and "one" encompasses the conventional meaning, and includes the meaning "one or more." Hence, a description of a microcapsule, or a pro-drug, for example, would include the meaning one or more as a particular context requires.

A gel to be used in the procedures of the present invention, e.g. to obtain microcapsules of a certain size, is a three dimensional network which has a random structure. Molecular sieve gels consist of cross-linked polymers that do not bind or react with the material being analyzed or separated. For gel filtration purposes, the gel material is generally uncharged. The space within the gel is filled with liquid and the liquid phase constitutes the majority of the gel volume. Materials commonly used in gel filtration columns include dextran, agarose and polyacrylamide.

Dextran is a polysaccharide composed of glucose residues and is commercially available under the names Sephadex (Pharmacia Fine Chemicals, Inc.). The beads are prepared with various degrees of cross-linking in order to separate different sized molecules by providing various pore sizes. The size of the cross-linking molecule can also be increased to obtain larger pore sizes. Alkyl dextran is cross-linked with N,N'-methylenebisacrylamide to from Sephacryl-S300 which allows strong beads to be made that fractionate in larger ranges than Sephadex can achieve.

Polyacrylamide is a polymer of cross-linked acrylamide prepared with N,N'-methylenebisacrylamide as the cross-linking agent. Polyacrylamide is available in a variety of pore sizes from Bio-Rad Laboratories (USA) to be used for separation of different size particles. For a discussion of gel chromatography, see Freifelder, Physical Biochemistry, Second Edition, pages 238–246, incorporated herein by reference.

A series of more than 38 separate experiments on four space flights has led to the development of aspects of this invention. These experiments along with their ground-based counterparts are described below for the purpose of pointing out the invention specifically and providing details useful in carrying out the invention. These specific examples, however, do not limit the scope of the claimed invention.

The inventors have demonstrated that methods of making microcapsules that use the preferred formulations of the present disclosure and that utilize vigorous mixing at Earth-normal gravity typically fail to form microcapsules of any kind. In some attempts, poorly formed microcapsules have been formed. Typically, these microcapsules will demonstrate considerable lack of sphericity, coalescence, and non-uniformity.

By contrast, when the methods of the invention are applied to form microcapsules, both in microgravity and under unit gravity at temperatures below ambient, numerous capsules may be formed, having both large and small diameters. Early studies showed that the microcapsules formed when the first phase was organic and when the first phase was aqueous. These studies demonstrated that uniformity and sphericity is a common characteristic of the microcapsules of the invention, regardless of the gravity environment. At higher magnification, these microcapsules, formed at unit gravity were discovered to comprise, in certain cases, several oil solvent spheroids nested inside a microcapsule, each of which oil solvent spheroids was surrounded by the inner aqueous layer.

Microcapsules formed under microgravity were made with a fluorescent dye in order to demonstrate the ability of the microcapsules of the invention to segregate a drug into a distinct layer. Viewing the microcapsules using a light source and optics to enable visualization of the fluorescent dye location, the internal spheroids and aqueous shell or layer were seen to fluoresce, indicating the location of the dye therein.

Other studies demonstrated the capacity of the methods of the invention to create spherical microcapsules of uniform and substantial volumes which are capable of forming crystalline structures in their internal layers or shells. The inventors made microcapsules with a single cubic crystal of Cis-platinum trapped within, as well as microcapsules with numerous crystals of Cis-Platinum formed within. The Cis-Platinum containing microcapsules were also treated to contain a radio-contrast oil (iodinated poppy seed oil).

FIG. 1 is a schematic drawing of the in situ activation of a drug or enzyme contained in a microcapsule. The microcapsule 120 has an outer polymer membrane 122 that encloses at least two immiscible liquid phases. A first internal, continuous phase 128 contains a prodrug or proenzyme 130, and a second internal, phase 124 contains an activating agent 126. Activating electromagnetic energy 132 is shown passing through the outer membrane 122 and causing the two phases 124, 128 to mix, bringing the activating agent 126 and the prodrug or proenzyme 130 into contact. This contact results in formation of an activated drug or enzyme 134 to which the outer membrane 122 is permeable allowing the drug or enzyme to diffuse out of the microcapsule 120.

The following examples are offered by way of illustration and are not intended to limit the scope of the invention in any manner. All of the materials used in these examples were obtained from well known commercial sources, or as specifically stated in the examples. Essentially conventional methods were employed in each instance where no specific procedure is stated.

EXAMPLE I

Microgravity Experiments Summary

The basic formulations and simplified liquid-liquid, dispersion methods were developed in 1988 and 1989. The conceptual approach is shown in FIG. 1. FIG. 1 is a schematic showing formation of a multi-lamellar microcapsule with an aqueous drug/oil dispersion at its center, a hydrocarbon/oil drug#2 and/or radiocontrast medium (e.g. IPO) as a next layer, an aqueous layer/drug (e.g., cis-platinum) as a next layer, and a polymeric outer coating or skin. Microencapsulation-related experiments designed to overcome the limitations of the first methods were conducted on six space missions beginning in April 1989 with the Consort-I sounding rocket using the Materials Dispersion Apparatus (MDA) mini-lab developed by Instrumentation Technology Associates, Inc. The sounding rocket flights produced only 6.5 minutes of microgravity conditions, but this was adequate to form the unique microcapsules in a single step. Experiments on the Space Shuttle permitted 10 minute dispersion times followed by curing of the outer polyglyceride skin for eight days under microgravity conditions. A summary of these experiments is shown in Table 2. New formulations were tested on Shuttle STS-52, using only aqueous-soluble drugs, polymers and surfactants, and on STS-56 using alcohols as co-surfactants. The specific experiments and results are described in detail in the examples to follow.

TABLE 2

MED Flight Experiments Summary

| MISSION | DATE | EXPERIMENTS | MATERIALS | RESULTS |
|---------|------|-------------|-----------|---------|
| Consort-1 | 4/89 | protein diffusion | urokinase & antibodies | diffusion rates established |
| Consort-1 | 3/90 | diffusion kinetics | urokinase & myoglobin | kinetics verified |
| Consort-4 | 11/91 | microencapsulation of drugs[a,b] | Cis-Platinum, amoxicillin, urokinase & Strept-avidin | multi-lamellar microcapsules w/ alternating hydrophilic & hydrophobic layers |
| Consort-5 | 9/92 | microencapsulation of drugs[a,b] | Cis-platinum, amoxicillin & urokinase | multi-lamellar microcapsules w/ alternating hydrophilic & hydrophobic layers |
| STS-52 | 10/92 | microencapsulation of drugs (aqueous polymers only)[a,b] | Cis-platinum, amoxicillin & urokinase | multi-lamellar microcapsules, crystals within microcapsules |
| STS-56 | 4/93 | microencapsulation of drugs (alcohol co-surfactants)[a,b] | Cis-platinum, amoxicillin & urokinase | multi-lamellar microcapsules, crystals within microcapsules |

[a]Fluorescent labels included
[b]Fluorescent beads included

EXAMPLE II

Gravity-Dependent Restrictions Recognized

Gravity-dependent restrictions in the basic liquid-liquid spontaneous microencapsulation process led to the design of several microgravity experiments to explore the utility of this process when density-driven phenomena were eliminated. In particular, density-driven, gravity-dependent restrictions of the liquid-liquid microencapsulation process were: early phase separation producing fragile microcapsules; interfacial dynamic flow causing coalescence of microcapsules. Failure of ground-based experiments to derive uniform microcapsules lead to a desire to attempt microcapsule formation in space.

The microgravity flight experiments led to the development of a new liquid-liquid microencapsulation process that involves use of surfactants and co-surfactants in the aqueous phase and co-surfactant alcohols in the organic phase, which also contained, in one embodiment, high molecular weight polymers that formed a tough outer "skin" on the final microcapsules. In microgravity, a single step dispersion produced unique multi-lamellar microcapsules containing various aqueous drags co-encapsulated with iodinated poppy seed oil (a radiocontrast medium with a sp. gravity= 1.35). Subsequent ground control experiments also produced some of these unique microcapsules and illustrated that the 1-g process could be improved to yield useable microcapsules by using different formulations. In particular, it became clear that the outer coatings substantially improved the ruggedness of the microcapsules formed.

EXAMPLE III

Sounding Rocket Experiments

Initial experiments on Consort-1 and -3 were used to determine the effective mixing and diffusion kinetics in the MDAs (see below for apparatus description). This showed that sufficient volume was mixed at the interface via diffusion to allow formation of microcapsules. These experiments also provided the diffusion constants for each of the components of the liquid phases.

The first successful microencapsulation of drugs in microgravity was conducted on the Consort-4 mission in November 1991. The microcapsules were recovered and analyzed by microscopic image analysis. Mono-dispersed fluorescent beads were included as internal size standards and fluorescent labels were used to determine the distribution of drug in the various fluid compartments. Additional experiments, conducted on Consort-5 in September 1992, confirmed the capabilities of the new method for forming multi-lamellar microcapsules with alternating layers of hydrophilic and hydrophobic drugs.

Microcapsules formed in 38 microgravity mini-experiments used liquid-liquid dispersion of aqueous drug solutions, surfactant and polyethylene glycol dispersed in alcoholic co-surfactant solutions containing soluble polyglycerides.

Microcapsules of both oil/water and polymer/water/oil were recovered from the Consort flights. These experiments produced multi-lamellar liquid microcapsules (concentric spheres within spheres) comprised of three or more, alternating immiscible layers. Image analysis of the microcapsules was made possible by co-encapsulation of standard size fluorescent beads. Microcapsules were formed in the ranges of 1–15 microns, 40–50 microns, 110–130 microns and 160–230 microns in diameters. This was a substantial improvement over the prior art approaches which had initially been attempted by the inventors to derive microcapsules only in the 10 micron and less range. The size distribution covered a range of from about as low as 5 microns in diameter up to about 300 microns in diameter and greater. The average size of the microcapsules formed in these experiments was about 150 microns, greatly in excess of the average 10 micron or less diameters obtained with prior art approaches.

The ruggedness of the microcapsules formed under these conditions allowed for size segregation by filtration or other separation methods. Digital image analysis (National Institutes of Health image analysis program) of phase contrast and fluorescent images taken with a fluorescent microscope also confirmed that the aqueous-soluble drugs were routinely encapsulated within the inner aqueous core and the outermost aqueous shell of the microcapsules.

Multi-lamellar microcapsules were also formed which contained relatively large amounts of EPO (Guerbet Laboratories-France, Savage Laboratories-U.S.A.) in discrete lamella, including microcapsules with IPO comprising up to 38% of the total volume. Often small hemispheres of IPO were also found clinging to the outer surface of the large inner (aqueous) sphere or adhered to the outer polymer skin of the microcapsule.

Microcapsules formed by almost all of the formulations survived 15-g accelerations, severe vibrations and turbulent mixing, during the reentry of the experiment capsule, and have remained intact for two years after recovery from space. These multi-layered microcapsules are similar to liquid-filled, thin-skinned, micro-balloons which are flexible enough to be manipulated on a microscope slide without collapse.

The microcapsules formed in just 6.5 minutes of microgravity retain their spherical shape and appear tough enough to survive the extensive physical manipulations required for sizing, final preparation and storage of parenteral suspensions, and the fluid shear encountered after intravascular injection. The inventors have also found that such microcapsules may form within a period of a few seconds.

Also formed were very unusual structures (multiple small spheres of aqueous-soluble drug) distributed within multi-lamellar o/w/o microcapsules, wherein the aqueous spheroids are arranged in an annular ring that appears fixed in a plane within the innermost sphere (not shown). These ring structures remain intact when the microcapsules are "rolled around" on the microscope slide without rupturing. These structures demonstrate the ability of the methods of the invention to form small spheroids that do not coalesce inside the larger microcapsule. Such structures may be advantageously used to control the specific volume to surface area ratio in order to control the rate of diffusion of a solute in such spheroids, for use in sustained release of pharmaceuticals contained in such spheroids, for example. These internal spheroids may also be used to maintain a physical separation between an activating agent and the prodrug, wherein rupture of the spherical membrane by the activation energy allows the activator to be exposed to the prodrug.

EXAMPLE IV

Space Shuttle Experiments

In experiments conducted on STS-52, the inventors co-encapsulated cis-platinum (diaminodichlor-cis-platinum; Bristol Laboratories) with IPO by forming microcapsules from water-soluble polymers using special formulations of aqueous, non-alcoholic solvents. Such formulations will find particular utility in co-encapsulations of anti-tumor compounds along with radiocontrast medium for tracking drugs in the body.

Polyvinyl pyrolidone (PVP), polyvinyl alcohol, and a commercial lecithin (Centrolex-F®; a phospholipid compound derived from soya and produced by U.S. Soya, Inc.) were used to form multi-lamellar microcapsules at 20° C. Fluorescent beads and fluorescent label were co-encapsulated with the drugs to permit drug-distribution measurements within the various lamellae, using fluorescence microscopy and digital image analysis. The final microcapsules were recovered and resuspended in either aqueous solutions, IPO or mineral oil. The microcapsules formed by these formulations were similar to those made using alcohol-soluble polyglycerides. However, without the hydrocarbon-soluble polymer membrane these microcapsules were more fragile and friable.

Another unique type of microcapsule was formed during these experiments that was characterized by drug crystals formed within the inner aqueous core of the multi-lamellar microcapsules. Microcapsules were formed which were packed (approximately 65% of the aqueous compartment) with crystals of Cis-platinum, an anti-tumor drug. Microcapsules containing crystals of amoxicillin were also formed in the STS-52 experiments. These illustrate that aqueous-soluble drugs can be encapsulated at very high concentrations near the solubility limit of the drug. After the microcapsules are formed the drug can become further concentrated (perhaps via the alcohol absorbing the water from the aqueous phase in which the pharmaceutical solute is dissolved) to form large crystals which are more stable than the dissolved drug during prolonged storage.

Microcapsules formed from first organic solvent/polymer methods appeared to be more rugged (by visual comparison under the microscope) than those formed on STS-52 formed from first solvent aqueous/polymer methods. The STS-56 experiments again produced multi-lamellar liquid microcapsules (multiple concentric spheres within spheres) comprised of alternating immiscible layers. Using fluorescent 6.4 micron beads and image analysis, it was found that the most interesting microcapsules were formed in the range of 10–15 micron, 40–50 micron, 50–100 micron, and 160–230 micron diameters. These diameter distributions were of particular interest since it is known that intraarterial uses can accommodate 50–300 micron diameter microcapsules while intravenous applications can only tolerate 1–10 micron microcapsules. Thus, by segregating the microcapsules into sized fractions (sieving), it should be possible to address particular intravascular limitations.

As noted above, microcapsules were formed containing crystals of cis-Platinum or amoxicillin. The crystals apparently were formed after encapsulation. Several microcapsules were formed that contained a single, large cubic crystal of Cis-Platinum which so completely filled the inner sphere that only about 15% of the inner volume remained as a liquid. One encapsulated, cubic Cis-Platinum crystal was measured at 48 microns across within a 57 micron diameter microcapsule. After formation, some of the microcapsules were dispersed in an external oil phase (either IPO or mineral oil) and allowed to cure for eight days before return to Earth.

These microgravity experiments have shown that formation of multi-lamellar, alternating-phase microcapsules can be controlled by proper timed-sequence exposures of the immiscible phases using special solvent formulations and surfactants. Once formed, these microcapsules remain spherical due to the predominant surface tension of the internal phases and polymer/solvent phase partitioning at the interfaces.

These experiments clearly demonstrated the capability to use liquid-liquid diffusion mixing to form unique microcapsules containing hydrophilic and hydrophobic drugs under microgravity conditions. Thus, ground-based experiments were conducted to compliment and replicate the space experiments. These ground-based experiments were able to replicate the size range (5–250 microns in diameter) to a limited degree, but the average size microcapsule obtained was about 10–40 microns in diameter. Still, this was a substantial improvement over the prior art approaches which rarely formed microcapsules over 10 microns in diameter. It was also observed that the ground-based experiments resulted in less rugged microcapsules. This is likely a result of the gravity-dependent deformations of the spherical microcapsules as they form giving rise to areas of thinner polymer deposition. Thus, the flexible microcapsules, formed under micro-gravity conditions, have more uniform size distributions than those formed in 1-g, are more rugged, and have a higher average diameter than ground-made microcapsules, largely due to the absence of thermal convection, buoyancy forces, and instabilities that occur at the immiscible interfaces.

The microgravity experiments illustrate the feasibility of co-encapsulating aqueous-soluble drugs, hydrocarbon-soluble drugs and oil-based contrast media within a lipid-soluble, polyglyceride outer film which cures rapidly enough to be impervious to oil or hydrocarbon resolubilization. They also allow the formation and harvesting of unique microcapsules which are durable enough to be removed from the external solvent without disruption or destruction of the internal phases. It is anticipated that these microcapsules will have several advantages over conventional liposomes that are designed for intravascular injection.

EXAMPLE V

Flight Hardware Description

The microencapsulation experiments described herein were conducted using the Materials Dispersion Apparatus (MDA; ITA, Inc., Exton, Pa.). The MDA's consist of an upper and a lower block that contain chambers for each sample fluid. The blocks are misaligned at launch so that the chambers are not in contact with each other. Upon activation in microgravity, the blocks are moved to align the chambers so that the fluids can mix by liquid-liquid diffusion. Some of the experiments were conducted with a single-step fluid mixing, and some were done with a two-step fluid mixing technique which allows diffusion of a third fluid or sample into the mixture of the first two fluids while still in the microgravity environment. In these experiments, the shear forces are minimal while moving the fluids into contact with each other.

EXAMPLE VI

Discussion and Alternative Embodiments

Spontaneous formation of multi-lamellar, microcapsules containing alternating layers of aqueous and hydrophobic solvent compartments is strongly dependent on the interfacial tension and the amount of mixing between immiscible liquid phases. On Earth this process is limited by gravity-dependent, density-driven separation of the immiscible liquids into stratified horizontal layers. In microgravity, this process is largely dependent on the surface-free energies of the different liquids, but independent of density-driven convection or buoyant phase separation. Hydrocarbon soluble, high molecular weight polymers have been included in the formulations to form flexible, permeable "skins" or outer coatings around the liquid microcapsules as they are created by phase partitioning mechanisms. It is also possible to form such polymer barriers between internal layers. The microcapsules can be formed and cured without deformation by contact with container walls.

More specifically, co-encapsulation of an aqueous-soluble, anti-tumor drug (Cis-platinum) and a radio-contrast medium (IPO), in microgravity, has produced a unique drug delivery system that can be visualized by radiologic or computerized tomography scanning to insure that the cytotoxic drug is delivered directly to the target tumor. Multi-layered microcapsules have been developed which can provide a new intravascular delivery system for targeted tissues and sequential, sustained release of multiple anti-tumor drugs. This method has resulted in formation of flexible spherical microcapsules of more uniform sizes, which can provide maximum packing densities and maximum drug delivery to target organs or tumors.

Multi-layered microcapsules can be designed to protect active forms of urokinase and other thrombolytic enzymes until they are delivered and entrapped at the local site of a blood clot, where therapeutic doses of the enzyme can diffuse out to dissolve the unwanted embolism. These immiscible-liquid diffusion methods also could be used for encapsulating certain labile drugs to make microcapsules for special purpose drug delivery systems, especially those designed to deliver drugs via the nasal or buccal mucosa or via inhalation directly to the lungs. Examples include protected delivery of mucolytic DNAse for sustained release treatment of cystic fibrosis and I anti-trypsin for patients with deficiencies in the lung epithelium.

EXAMPLE VIII

Redispersion of Microcapsules in Aqueous or Oil Vehicles

A frequently used second step includes dispersion of the microcapsules (after they have formed) in different aqueous/polymer solvents or in a pure oil phase. A unique attribute of microcapsules formed by these methods is that they do not re-dissolve in an oily external phase, even though the semi-permeable outer skin is hydrophobic. This produces a suspension in the liquid carriers that are commonly used for intravascular administration.

Examples of suitable aqueous solutions for redispersion would include, but not be limited to dextran, PEG, phosphate buffered saline (PBS), Ringer's solution, or any solution known in the art that is selected so the membrane has little or no solubility in that medium. The solutions are sterilized prior to redispersion and are selected for the particular application, such as injection into a human. It is a further advantage, that redispersion in these solutions inhibits coalescence.

EXAMPLE IX

Exemplary First Organic Solvent Microcapsule Formulations

The following formulations have been used with particular success by the inventors in both Earth-normal and microgravity methods of making microcapsules.

Fluid 1-(hydrocarbon). The first solvent is a hydrocarbon fluid (ethyl alcohol, methyl alcohol, or isopropyl alcohol) with a low or medium HLB (HLB=5–10). One or more co-solvents are used (which also can act as co-surfactants).

Small concentrations of oil and water are added. Into this mixture, the mono- or polyglyceride is dissolved up to 5% w/v. An example is:

88% IPA
2.5% m-Hexanol
2.5% n-Heptanol
5% IPO
2% H$_2$O
5% GMS

Fluid 2 (aqueous). The second solvent is water plus surfactants (ex. polyethoxylated sorbitan esters; polyethylene glycol). A polysaccharide (Dextran) and normal saline (0.9%) are added which helps achieve the desired critical micelle concentration. A pharmaceutical soluble in water is added. An example is:

1% PEG 4000
5% Dextran-40 (MW=40,000)
0.9% Sodium chloride
2% Sorbitan Monooleate/20 moles Ethylene oxide
Water (up to 100% volume)
dissolved drug at specified concentration
(according to required dose and release rate)

Fluid 3 (oil). An oil, immiscible with the first two fluids in which the microcapsule's "outer skin" is insoluble so that the suspended microcapsules can be delivered by injection when non-aqueous administration is required. Submersion of microcapsules in the oil also can aid the curing or polymerization of the "outer skin." A preferred example of the oil vehicle is halogenated poppy seed oil which also serves as a radiocontrast medium.

Alternate compositions for Fluid 1
Main solvent-ethyl alcohol
Co-solvents-(co-surfactants) are normal alcohols- C4 to C8
  high dielectric constant solvents-
    tetrahydrofuran
    dioxane
    acetonitrile
    dimethylformamide
    dimethylacetamide
    dimethylsulfoxide
Oil-dense radiocontrast liquids s.a. halogenated unsaturated oils
  e.g. halogenated poppy seed oil, cotton seed oil, safflower oil, olive oil, canola oil, peanut oil, sesame oil, corn oil.
    also saturated oils can be used, s.a. heavy mineral oil, liquid petrolatum
Polymers-used to form the "outer skin" on the microcapsules
  monoglycerides, polyglycerides—esp. glycerol esters ranging from C12–C22,
    e.g. monostearate, distearates, monooleates, monolaurates and olive oil
polyglycerides-cholesterol, waxy plant sterols (stigmasterol, phytosterol, campesterol)
    phospholipids-lecithins (phosphatydyl choline) and/or combinations with mono/polyglycerides
  polyvinylpyrrolidone
  polyacrylates,
  PEG-hydroxypropyl methacrylate (HPMA)
  PEG 4,000–12,000
    polyethylene glycol/acrylate copolymers
    polyethylene glycol/dextran copolymers Alternate concentrations:

| Fluid 1: | Main solvent | 75–95% |
|---|---|---|
| | Co-solvents | 1–10% |
| | Oil | 1–10% |
| | Polymer | 1–5% |
| | Water | 1–20% |

Alternate composition for Fluid 2
  PEG 200–20,000
  Dextran-40 (MW=40,000–100,000)
  0.9% Sodium chloride
  Sorbitan Monolaurate/20 moles Ethylene oxide
  balance is water
  Drug dissolved at saturated or specified concentration (according to required dose and release rate)
Alternate concentrations:
  PEG 1–5%
  Dextran (MW=40,000–100,000) 5–10%
  Sodium chloride 0.9%
  Sorbitan Monolaurate/20 ETO1–5%
  Water (balance of volume)
  Drug concentration saturated or specified
Alternate composition for Fluid 3
  Dense radiocontrast liquids s.a. iodinated unsaturated oils e.g. poppy seed oil, cotton seed oil, safflower oil, olive oil, canola oil, peanut oil, sesame oil, corn oil.
  Also saturated oils can be used, s.a. heavy mineral oil and petrolatum.
  One hundred percent oil or a mixture may be used as a carrier vehicle for the suspended microcapsules.

EXAMPLE X

Exemplary First Aqueous Solvent Microcapsule Formulations

Alternate Method-Hydrophilic Outer Skin
Fluid 1-(aqueous); the main solvent is a water, one or more co-solvents (which also can act as co-surfactants), and lecithins are dissolved up to 5% w/v to form the outer skin on the microcapsules.
  An example is: 3% polyvinyl alcohol dissolved in a mixture of 20% isopropyl alcohol and 80% water
Fluid 2 (aqueous); the main solvent is water plus surfactants (ex. polyethoxylated sorbitan esters; polyethylene glycol) and plus a polysaccharide (Dextran) and normal saline (0.9%) which helps achieve the desired critical micelle concentration.
  An example is:
  1% PEG 4000
  5% Dextran-70 (MW=70,000)
  0.9% Sodium chloride
  2% Sorbitan Monooleate/20 moles Ethylene oxide
  Water (up to 100% volume)
  dissolved drug at saturated or specified concentration (according to required dose and release rate)
Fluid 3 (aqueous)-a PEG and PVP solution which can aid the curing or polymerization of the "outer skin."
  1% Polyvinyl pyrollidone
  4% PEG 4000
  5% Dextran-70 (MW=70,000)
  balance is 0.9% Sodium chloride

EXAMPLE XI

An example of a microcapsule, suitable for in situ activation of a prodrug is shown schematically in FIG. 1. In this embodiment the prodrug, floxuridine for example, may be contained in the continuous, internal aqueous phase. The activator, thymidine kinase is also contained within the microcapsule. During irradiation with ultraviolet light of 300–390 nanometers, the internal liquid phases in the microcapsules exhibit a spontaneous, vigorous mixing action with brings the contents of the two phases together, and increases the activation kinetics of the water soluble floxuridine to the water insoluble active form 5-FU, which diffuses out of the microcapsule.

EXAMPLE XII

The following example describes an embodiment of the invention, in which microcapsules containing an active agent and an activator are subjected to an electromagnetic field, and the electromagnetic field is effective to release free radicals or ions that change the state of an agent within the microcapsule. In this example, the microcapsules contain eosin-Y and PEG-diacrylate. Upon irradiation, eosin-Y is activated to release free radicals, which then activate the PEG-diacrylate to gellation.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, one alternate embodiment includes use of aqueous-soluble cyclodextrin (in the hydrophilic phase) which has a hydrophobic center that can itself entrap hydrophobic drugs thereby acting as a carrier for hydrophobic drugs within the aqueous phase. Another alternate embodiment allows after microcapsules are formed, for ancillary polymeric outer coats to be applied by conventional methods (electrostatic coating, aerosolization and drying, etc.). This is made possible by designing the precise chemical makeup of the initial polymeric outer skin such that it will be compatible with both drug diffusion and the ancillary coating to be applied. When surfactants are used to facilitate adhesion of the third solution or ancillary coating the HLB must be selected to be compatible with the HLB of the existing outer coating which has already been formed, such that the solution containing the ancillary coating will wet the surface of the existing outer coating, to enable deposition of the ancillary coating. This is in contrast to conventional liposomes whose outer membrane composition is a variable, depending on the phase separation of the phospholipids and cholesterol adduct when each liposome forms. Another alternative embodiment incorporates an energy absorbing medium (e.g. photoactivator) which can absorb electromagnetic, ultraviolet, infrared, ultrasonic, radiofrequency and microwave radiation and thereby cause activation of a short-lived drug component just prior to administration or after the microcapsules have reached the target site. Another embodiment incorporates magnetic particles and magnetic fields or free-fluid electrophoretic mechanisms, etc. to facilitate dispersion or transport of one phase across the immiscible interface into the other phase. This has been demonstrated as a single pass, unidirectional form of mixing that is best exploited in microgravity. Another embodiment includes attachment of certain (hydrophobic) antibodies to the polymeric skin which gives the microcapsules site specificity by being able to bind to target cells (e.g. tumor) while entrapped drugs diffuse out to provide maximum doses to those cells with that antigenic site. Another embodiment makes use of polyethylene glycol (PEG) complexed to peptide or protein drugs and a customized polymeric outer skin which permits the drug-PEG complex to diffuse out of the microcapsule as an intact entity. This permits the drug to resist antibody attachment and remain in the blood stream longer as found in the Pegnology 4 type of drug complexes developed by Enzon, Inc. The improvement being delivery of this complex in the tailored microcapsules and controlled release of the complex through the specially designed polymeric outer skin. Another embodiment is microcapsules containing magnetic particles that can be heated by exposure to an electromagnetic field so that the particles are able to melt the polymer shell and release the contents without causing widespread hyperthermic damage to the surrounding tissues. Other embodiments include the use of the microcapsules of the invention for the production of crystals within an internal aqueous phase. All such modifications are intended to be included within the scope of the appended claims.

While the preferred embodiments of the invention have been shown and described, modifications thereof can be made by one skilled in the art without departing from the spirit and teachings of the inventions. The embodiments described herein are exemplary only, and are not limiting. Many variations and modifications of the invention and apparatus disclosed herein are possible and are within the scope of the inventions. Accordingly, the scope of protection is not limited by the description set out above, but is only limited by the claims which follow, that scope including all equivalents of the subject matter of the claims.

All patents and publications mentioned in this specification are indicative of the level of skill of those of knowledge in the art to which the invention pertains. All patents and publications referred to in this application are incorporated herein by reference to the same extent as if each was specifically indicated as being incorporated by reference and to the extent that they provide materials and methods not specifically shown.

REFERENCES CITED

The following references to the extent that they provide procedural details supplementary to those set forth herein, are specifically incorporated herein by reference.

Allen, T. M., Interactions of Drug Carriers with the Mononuclear Phagocytic System, in G. Gregoriadis (Ed.) *Liposomes as Drug Carriers,* John Wiley & Sons Ltd., New York pp.37–50, 1988.

Allen, T. M., Mehra, T., Hansen, C. and Chin, Y. C., Stealth Liposomes: An Improved Sustained Release System for 1-b-D-Arabinofuranosylcytosine, Cancer Res. 52:2431–39, 1992.

Bhargava, H. N., Narurkar, A., and Lieb, L. M., Using Microemulsions for Drug Delivery, Pharmaceutical Technology, pp. 46–54, March 1987.

Chang, T. M. S., The in vivo effect of semi-permeable microcapsules containing L-asparaginase on 6C3HED lymphosarcoma, Nature, 229:117–178, 1971.

Gabizon, A., et al., Liposome-Associated Doxorubicin: Preclinical Pharmacology and Exploratory Clinical Phase, in G. Lopez-Berestein and I. J. Fidler (Eds.) *Therapy of Infectious Diseases and Cancer,* Alan R. Liss, Inc., New York, pp. 189–203, 1992.

Halbert, G. W., Stuart, J. B., Florence, A. T., The Incorporation of Lipid Soluble Antineoplastic Agents into Microemulsions-Protein-free Analogues of Low Density Lipoprotein, Int. J. Pharm. 21: 219–232, 1984.

Hand, J. W., Biophysics and Technology of Electromagnetic Hyperthermia, in Gauthereie, M., (Ed.) *Methods of External Hyperthermic Heating,* Springer-Verlag, New York, pp. 16–24, 1991.

Kimler, B. F, et al., Combination of Aziridinylbenzoquinone and Cis-platinum with Radiation Therapy in the 9L Rat Brain Tumor Model, Int. J. Radiation Oncology Biol. Phys, 26: 445–450, 1993.

Magin, R. L., Hunter, J. M., Meisman, M. R., and Bark, G. A., Effect of vesicle size on clearance, distribution and tumor uptake of temperature sensitive liposomes, Cancer Drug Delivery 3:223–237, 1986.

McCutcheon's Detergents and Emulsifiers, 1979, North American Edition, McCutcheon Division, MC Publishing Co., 175 Rock Road, Glen Rock, N.J. 07452.

Mitchell, J. B., Cook, J. A., and Russo, A., Biological Basis for Phototherapy, in Morstyn, G. and Kaye, A. H. (Eds.), *Phototherapy of Cancer,* Harwood Academic Pub., New York, pp.1–22, 1990.

Parikl, 1. and Stern, W. Microcrystal® Drug Delivery System, in Harvey S. Price (Ed) *The Biotechnology Report* 1993/94, Bookbuilders, Ltd., Hong Kong, pp. 219–220, 1994.

Talsma, H. and Crommelin, D. J. A., Liposomes as Drug Delivery Systems, Part 1: Preparation. Pharmaceutical Technology, pp. 96–106, October 1992.

Wright, K. C., Wallace, S., Mosier, B. and Mosier, D., Microcapsules for Arterial Chemoembolization: Appearance and In Vitro Drug Release Characteristics, J. Microencapsulation 5:13–20, 1988.

What is claimed is:

1. A method of in situ activation of a drug comprising:
   providing a microcapsule wherein the microcapsule comprises two or more internal liquids, wherein each internal liquid is immiscible with the other internal liquids, and all of the internal liquids are enclosed together in a single polymer shell, a drug precursor associated with at least one internal liquid phase; and
   exposing the microcapsule to an energy source in an amount effective to promote physical mixing of the immiscible liquid phases and to increase the activation kinetics of activation of the drug precursor.

2. The method of claim 1, wherein one of said internal liquid phases is an aqueous phase and one of said internal liquid phases is a hydrocarbon or oil phase.

3. The method of claim 2, wherein said aqueous phase is in contact with the polymer membrane.

4. The method of claim 2, wherein said hydrocarbon or oil phase is in contact with the polymer membrane.

5. The method of claim 3, wherein the drug precursor is more soluble in the hydrocarbon or oil phase than in the aqueous phase and the activated drug is more soluble in the aqueous phase than in the hydrocarbon or oil phase.

6. The method of claim 4, wherein the drug precursor is more soluble in the aqueous phase than in the hydrocarbon or oil phase and the activated drug is more soluble in the hydrocarbon or oil phase than in the aqueous phase.

7. A method of in situ activation of a drug comprising:
   providing a microcapsule wherein the microcapsule comprises two or more internal immiscible liquid phases enclosed in a polymer shell, a drug precursor associated with at least one internal liquid phase; and
   exposing the microcapsule to an energy source in an amount effective to promote physical mixing of the immiscible liquid phases and to increase the activation kinetics of activation of the drug precursor,
   wherein one of said internal liquid phases is an aqueous phase and one of said internal liquid phases is a hydrocarbon or oil phase,
   wherein said aqueous phase is in contact with the polymer membrane,
   wherein the drug precursor is more soluble in the hydrocarbon or oil phase than in the aqueous phase and the activated drug is more soluble in the aqueous phase than in the hydrocarbon or oil phase,
   wherein the pair consisting of said drug precursor and drug is chosen from the group consisting of papaverine and papaverine HCl, genoscopolamine and scopolamine, hematoporphyrin and dihematoporphyrin ester, and sulfamerazine sulfate and 2-sulfanilamido-4-methylpyrimidine.

8. A method of in situ activation of a drug comprising:
   providing a microcapsule wherein the microcapsule comprises two or more internal immiscible liquid phases enclosed in a polymer shell, a drug precursor associated with at least one internal liquid phase; and
   exposing the microcapsule to an energy source in an amount effective to promote physical mixing of the immiscible liquid phases and to increase the activation kinetics of activation of the drug precursor,
   wherein one of said internal liquid phases is an aqueous phase and one of said internal liquid phases is a hydrocarbon or oil phase,
   wherein said hydrocarbon or oil phase is in contact with the polymer membrane,
   wherein the drug precursor is more soluble in the aqueous phase than in the hydrocarbon or oil phase and the activated drug is more soluble in the hydrocarbon or oil phase than in the aqueous phase,
   wherein the pair consisting of the drug precursor and the drug is chosen from the group consisting of floxuridine and 5-fluorouracil, cocaine hydrochloride and cocaine base, and estrone and estradiol.

9. A method of in situ activation of a drug comprising:
   providing a microcapsule wherein the microcapsule comprises two or more internal immiscible liquid phases enclosed in a polymer shell, a drug precursor associated with at least one internal liquid phase; and
   exposing the microcapsule to an energy source that causes the precursor to assume an active state,
   wherein the pair consisting of said drug precursor and the drug is chosen from the group consisting of dehydrocholesterol and vitamin $D_3$, testosterone acetate and testosterone, ergosterol and vitamin $D_2$, nitromethane and 1-methyl-2(1-hydroxy-1 methylethyl) diazene, and α, α-dinitroketone and a diketone.

10. A micromixer useful for mixing two or more immiscible liquid phases contained in the micromixer comprising:
    a microcapsule comprising two or more immiscible internal liquid phases enclosed in a polymer shell and a radiant energy source effective to generate liquid flow within the microcapsule,
    said microcapsule formed by a method comprising:
      formulating a first phase comprising a first solvent, a first polymer soluble in said first phase and immiscible in a second phase, a co-solvent, oil, and water;
      formulating said second phase immiscible with said first phase, said second phase comprising a second solvent, a second polymer soluble in said second phase and immiscible in said first phase, a surface active agent, and a salt;
      said surface active agent having a hydrophilic/lipophilic balance value greater than that of said first polymer;

said second polymer having a hydrophilic/lipophilic balance value lower than that of said surface active agent;

creating an interface between said first and second phases in a manner that limits fluid shear, and maintains adsorptive surface characteristics at said interface.

11. A composition comprising a drug or drug precursor contained in a microcapsule comprising two or more concentric, immiscible internal liquid phases enclosed in a polymer shell, wherein a first of said internal liquid phases is in contact with said polymer shell, and wherein a second of said internal liquid phases is separated from said polymer shell by said first internal liquid phase, and further wherein said drug or drug precursor is associated with said second internal liquid phase, wherein said microcapsule is formed by a method comprising:

formulating a first phase comprising a first solvent, a first polymer soluble in said first phase and immiscible in a second phase, a co-solvent, oil, and water;

formulating said second phase immiscible with said first phase, said second phase comprising a second solvent, a second polymer soluble in said second phase and immiscible in said first phase, a surface active agent, and a salt;

said surface active agent having a hydrophilic/lipophilic balance value greater than that of said first polymer;

said second polymer having a hydrophilic/lipophilic balance value lower than that of said surface active agent;

creating an interface between said first and second phases in a manner that limits fluid shear, and maintains adsorptive surface characteristics at said interface.

12. The method of claim 9, wherein said drug precursor is dehydrocholesterol and the drug is vitamin $D_3$.

13. The method of claim 9, wherein said drug precursor is testosterone acetate and the drug is testosterone.

14. A method of in situ activation of a drug comprising:

providing a microcapsule wherein the microcapsule comprises two or more internal immiscible liquid phases enclosed in a polymer shell, a drug precursor associated with at least one internal liquid phase; and exposing the microcapsule to an energy source in an amount effective to promote physical mixing of the immiscible liquid phases and to increase the activation kinetics of activation of the drug precursor, wherein the microcapsule also contains a radiocontrast media.

15. The method of claim 14, wherein the radiocontrast media is a halogenated oil.

16. The method of claim 15 wherein the radiocontrast media is an oil selected from the group consisting of halogenated poppy seed oil, cotton seed oil, soybean oil, safflower oil, corn oil, sesame seed oil, and canola oil.

17. A method of in situ activation of a drug comprising:

providing a microcapsule wherein the microcapsule comprises two or more internal immiscible liquid phases enclosed in a polymer shell, a drug precursor associated with at least one internal liquid phase; and exposing the microcapsule to an energy source in an amount effective to promote physical mixing of the immiscible liquid phases and to increase the activation kinetics of activation of the drug precursor, wherein the drug precursor is a proenzyme.

18. A method of in situ activation of a drug comprising:

providing a microcapsule wherein the microcapsule comprises two or more internal immiscible liquid phases enclosed in a polymer shell, a drug precursor associated with at least one internal liquid phase; and exposing the microcapsule to an energy source in an amount effective to promote physical mixing of the immiscible liquid phases and to increase the activation kinetics of activation of the drug precursor, wherein the drug precursor is selected from the group consisting of a pro-thrombolytic enzyme, a pro-urokinase and a pro-tissue plasminogen activator.

19. The method of claim 1 wherein the energy source is selected from the group consisting of ultraviolet light, near infrared light, an electromagnetic field, radiofrequency, and microwave radiation.

20. A method of in situ activation of a drug comprising:

providing a microcapsule wherein the microcapsule comprises two or more internal immiscible liquid phases enclosed in a polymer shell, a drug precursor associated with at least one internal liquid phase; and exposing the microcapsule to an energy source in an amount effective to promote physical mixing of the immiscible liquid phases and to increase the activation kinetics of activation of the drug precursor, wherein the energy is near infrared light of about 700–900 nanometer wavelength.

21. A method of in situ activation of a drug comprising:

providing a micro capsule wherein the microcapsule comprises two or more internal immiscible liquid phases enclosed in a polymer shell, a drug precursor associated with at least one internal liquid phase; and exposing the microcapsule to an energy source in an amount effective to promote physical mixing of the immiscible liquid phases and to increase the activation kinetics of activation of the drug precursor, wherein the energy is ultraviolet light of about 220–390 nanometer wavelength.

22. A method of in situ activation of a drug comprising:

providing a microcapsule wherein the microcapsule comprises two or more internal immiscible liquid phases enclosed in a polymer shell, a drug precursor associated with at least one internal liquid phase; and exposing the microcapsule to an energy source in an amount effective to promote physical mixing of the immiscible liquid phases and to increase the activation kinetics of activation of the drug precursor, further defined as comprising administering said microcapsules to a subject, allowing said microcapsules to reach a target site and applying said energy to the subject.

23. The method of claim 22, wherein the location of the microcapsules is detected by a radio image.

24. The method of claim 22, wherein administration is intraarterial, intravenous or intraperitoneal.

25. The method of claim 22, wherein the microcapsules at least partially occlude a blood vessel.

26. The method of claim 22, wherein the energy is applied using an intravascular device.

27. The method of claim 26, wherein the intravascular device is a catheter.

28. The method of claim 26, wherein the energy is applied via a fiber optic conductor.

29. The method of claim 26, wherein the energy is applied via an electromagnetic transducer contained in an intravascular device.

30. The method of claim 1, wherein the microcapsule is from about 1 to about 500 microns in diameter.

31. The method of claim 1, wherein the microcapsule is from about 300 to about 500 microns in diameter.

32. The method of claim 1, wherein the microcapsule is from about 50 to about 300 microns in diameter.

33. The method of claim 1, wherein the microcapsule is from about 30 to about 50 microns in diameter.

34. The method of claim 1, wherein the microcapsule is from about 20 to about 30 microns in diameter.

35. The method of claim 1, wherein the microcapsule is from about 1 to about 20 microns in diameter.

36. A method of in situ activation of a drug comprising:
   providing a microcapsule wherein the microcapsule comprises two or more internal immiscible liquid phases, wherein neither internal immiscible liquid phase is enclosed separately by a polymer shell but wherein the internal immiscible liquid phases are enclosed together in a single polymer shell, a drug precursor associated with at least one internal liquid phase; and
   exposing the microcapsule to an energy source that causes the precursor to assume an active state.

37. The method of claim 36, wherein the drug precursor is activated by a oxidation, a reduction, a hydrolysis or a dehydrogenation reaction.

38. A composition comprising a drug or drug precursor contained in a microcapsule consisting of two or more concentric, immiscible internal liquid phases, wherein neither internal immiscible liquid phase is enclosed separately by a polymer shell but wherein the internal immiscible liquid phases are enclosed together in a single polymer shell, wherein a first of said internal liquid phases is in contact with said polymer shell, and wherein a second of said internal liquid phases is separated from said polymer shell by said first internal liquid phase, and further wherein said drug or drug precursor is associated with said second internal liquid phase.

39. The composition of claim 38, wherein said first internal liquid phase is an aqueous phase.

40. The method of claim 9, wherein said drug precursor is ergosterol and the drug is vitamin $D_2$.

41. The method of claim 9, wherein the drug precursor is nitromethane and the drug is 1-methyl-2(1-hydroxy-1 methylethyl) diazene.

42. The method of claim 9, wherein the drug precursor is α, α-dinitroketone and the drug is a diketone.

43. A method of in situ activation of a drug comprising:
   providing a microcapsule wherein the microcapsule comprises two or more internal immiscible liquid phases enclosed in a polymer shell, a drug precursor associated with at least one internal liquid phase; and
   exposing the microcapsule to an energy source that causes the precursor to assume an active state,
   wherein the microcapsule also contains a radiocontrast media.

44. A method of in situ activation of a drug comprising:
   providing a microcapsule wherein the microcapsule comprises two or more internal immiscible liquid phases enclosed in a polymer shell, a drug precursor associated with at least one internal liquid phase; and
   exposing the microcapsule to an energy source that causes the precursor to assume an active state,
   wherein the microcapsule contains the radiocontrast media a halogenated oil.

45. The method of claim 44, wherein the radiocontrast media is selected from the group consisting of halogenated poppy seed oil, cotton seed oil, soybean oil, safflower oil, corn oil, sesame seed oil, and canola oil.

46. The method of claim 36, wherein the energy source is ultraviolet light or near infrared light.

47. A method of in situ activation of a drug comprising:
   providing a microcapsule wherein the microcapsule comprises two or more internal immiscible liquid phases enclosed in a polymer shell, a drug precursor associated with at least one internal liquid phase; and
   exposing the microcapsule to an energy source that causes the precursor to assume an active state,
   wherein the energy source is near infrared light of about 700–900 nanometer wavelength.

48. A method of in situ activation of a drug comprising:
   providing a microcapsule wherein the microcapsule comprises two or more internal immiscible liquid phases enclosed in a polymer shell, a drug precursor associated with at least one internal liquid phase; and
   exposing the microcapsule to an energy source that causes the precursor to assume an active state,
   wherein the energy source is ultraviolet light of about 220–390 nanometer wavelength.

49. A method of in situ activation of a drug comprising:
   providing a microcapsule wherein the microcapsule comprises two or more internal immiscible liquid phases enclosed in a polymer shell, a drug precursor associated with at least one internal liquid phase; and
   exposing the microcapsule to an energy source that causes the precursor to assume an active state,
   further defined as comprising administering said microcapsules to a subject, allowing said microcapsules to reach a target site and applying said energy to the subject.

50. The method of claim 49, wherein the location of the microcapsules is detected by a radio image.

51. The method of claim 49, wherein administration is intraarterial, intravenous or intraperitoneal.

52. The method of claim 49, wherein the microcapsules at least partially occlude a blood vessel.

53. The method of claim 49, wherein the energy is applied using an intravascular device.

54. The method of claim 53, wherein the intravascular device is a catheter.

55. The method of claim 53 wherein the energy is applied via a fiber optic conductor.

56. The method of claim 53 wherein the energy is applied via an electromagnetic transducer contained in an intravascular device.

57. The method of claim 36, wherein the microcapsule is from about 1 to about 500 microns in diameter.

58. The method of claim 36, wherein the microcapsule is from about 300 to about 500 microns in diameter.

59. The method of claim 36, wherein the microcapsule is from about 50 to about 300 microns in diameter.

60. The method of claim 36, wherein the microcapsule is from about 30 to about 50 microns in diameter.

61. The method of claim 36, wherein the microcapsule is from about 20 to about 30 microns in diameter.

62. The method of claim 36, wherein the microcapsule is from about 1 to about 20 microns in diameter.

63. A micromixer useful for mixing two or more immiscible liquid phases contained in the micromixer comprising:
   a microcapsule consisting of two or more immiscible internal liquid phases, wherein neither internal immiscible liquid phase is enclosed separately by a polymer shell but wherein the internal immiscible liquid phases are enclosed together in a single polymer shell and a radiant energy source effective to generate liquid flow within the microcapsule.

64. The micromixer of claim 63, wherein said internal liquid phases include an aqueous phase and a hydrocarbon or oil phase.

65. The micromixer of claim 63, wherein the energy source is selected from the group consisting of a source of ultraviolet light, an electromagnetic field, a radiofrequency, or microwave energy.

66. A micromixer useful for mixing two or more immiscible liquid phases contained in the micromixer comprising:

a microcapsule comprising two or more immiscible internal liquid phases enclosed in a polymer shell and a radiant energy source effective to generate liquid flow within the microcapsule, wherein the energy source is a source of ultraviolet light at 220 to 390 nanometers wavelength.

67. The micromixer of claim 64, wherein said micromixer comprises a reactant associated with an aqueous phase and a different reactant associated with a hydrocarbon or oil phase, wherein said reactants produce a chemical reaction upon contact and wherein said mixing increases the reaction kinetics of the reaction.

68. The composition of claim 38, wherein said first internal liquid phase is a hydrocarbon or oil phase.

69. The composition of claim 38, wherein said composition is contained in a light protective container.

70. The method of claim 7, wherein said drug precursor is papaverine and the drug is papaverine HCl.

71. The method of claim 7, wherein said drug precursor is genoscopolamine and the drug is scopolamine.

72. The method of claim 7, wherein said drug precursor is hematoporphyrin and the drug is dihematoporphyrin ester.

73. The method of claim 7, wherein said drug precursor is sulfamerazine sulfate and the drug is 2-sulfanilamido-4-methylpyrimidine.

74. The method of claim 8, wherein the drug precursor is floxuridine and the drug is 5-fluorouracil.

75. The method of claim 8, wherein the drug precursor is cocaine hydrochloride and the drug is cocaine base.

76. The method of claim 8, wherein the drug precursor is estrone and the drug is estradiol.

* * * * *